United States Patent
Li et al.

(10) Patent No.: US 11,412,977 B2
(45) Date of Patent: Aug. 16, 2022

(54) SYSTEMS AND METHODS FOR QUANTITATIVELY CHARACTERIZING ALZHEIMER'S DISEASE RISK EVENTS BASED ON MULTIMODAL BIOMARKER DATA

(71) Applicant: THE MEDICAL COLLEGE OF WISCONSIN, INC., Milwaukee, WI (US)

(72) Inventors: Shi-Jiang Li, Brookfield, WI (US); Guangyu Chen, Brookfield, WI (US); Gang Chen, Wauwatosa, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 821 days.

(21) Appl. No.: 16/062,799

(22) PCT Filed: Dec. 15, 2016

(86) PCT No.: PCT/US2016/066928
§ 371 (c)(1),
(2) Date: Jun. 15, 2018

(87) PCT Pub. No.: WO2017/106498
PCT Pub. Date: Jun. 22, 2017

(65) Prior Publication Data
US 2021/0212629 A1     Jul. 15, 2021

Related U.S. Application Data

(60) Provisional application No. 62/268,051, filed on Dec. 16, 2015.

(51) Int. Cl.
    *A61B 5/00*     (2006.01)
    *G16H 15/00*     (2018.01)
    (Continued)

(52) U.S. Cl.
    CPC .......... *A61B 5/4088* (2013.01); *A61B 5/0263* (2013.01); *A61B 5/4842* (2013.01); *A61B 5/7275* (2013.01); *G01R 33/4806* (2013.01); *G01R 33/56341* (2013.01); *G01R 33/56366* (2013.01); *G16H 15/00* (2018.01); *G16H 50/30* (2018.01); *G16B 20/00* (2019.02)

(58) Field of Classification Search
    CPC ........................... A61B 5/4088; A61B 5/0263
    See application file for complete search history.

(56) References Cited

U.S. PATENT DOCUMENTS

2013/0116540 A1*    5/2013    Li .......................... G16H 50/70
                                                                                           600/410

OTHER PUBLICATIONS

Fonteijn et al. "An event-based model for disease progression and its application in familial Alzheimer's disease and Huntington's disease" (Year: 2012).*

(Continued)

*Primary Examiner* — Joseph M Santos Rodriguez
(74) *Attorney, Agent, or Firm* — Quarles & Brady LLP

(57) ABSTRACT

Systems and methods are described for computing a quantitative index that characterizes Alzheimer's disease ("AD") risk events based on a temporally ordered sequence of biomarker events. In general, the systems and methods described here implement a modified event-based probabilistic ("EBP") model to calculate the risk index from biomarker data.

14 Claims, 23 Drawing Sheets

(51) Int. Cl.
*G16H 50/30* (2018.01)
*A61B 5/026* (2006.01)
*G01R 33/48* (2006.01)
*G01R 33/563* (2006.01)
*G16B 20/00* (2019.01)

(56) References Cited

OTHER PUBLICATIONS

Young et al. "Adata-driven model of biomarker changes in sporadic Alzheimer's disease" (Year: 2014).*

Calabrese et al. "A Diffusion MRI Tractography Connectome of the Mouse Brain and Comparison with Neuronal Tracer Data" (Year: 2015).*

* cited by examiner

SYSTEMS AND METHODS FOR QUANTITATIVELY CHARACTERIZING ALZHEIMER'S DISEASE RISK EVENTS BASED ON MULTIMODAL BIOMARKER DATA

CROSS-REFERENCE TO RELATED APPLICATIONS

This application represents the national stage entry of PCT International Application No. PCT/US2016/066928 filed on Dec. 15, 2016, which claims the benefit of U.S. Provisional Patent Application Ser. No. 62/268,501, filed on Dec. 16, 2015, and entitled "Systems and Methods for Quantitatively Characterizing Alzheimer's Disease Risk Events Based on Multimodal Biomarker Data," all of which are herein incorporated by reference in their entirety.

STATEMENT REGARDING FEDERALLY SPONSORED RESEARCH

This invention was made with government support under AG020279 and AG035405 awarded by the National Institutes of Health. The government has certain rights in the invention

BACKGROUND OF THE DISCLOSURE

The field of the present disclosure is systems and methods for medical image and data processing. More particularly, the present disclosure describes systems and methods for processing medical images and data to generate a quantitative index value that characterizes Alzheimer's Disease risk events.

Current literature regards sporadic Alzheimer's disease ("AD") as a clinical entity arising from a series of pathophysiological events related to amyloidosis and neurodegeneration. These events, measured by corresponding AD biomarkers, are believed to occur in a temporally ordered manner along with disease progression; however, a detailed sequence remains ambiguous. Disentangling the temporal relationship among AD biomarkers provides insight into the evolution of AD pathogenesis. From a clinical perspective, an established AD biomarkers sequence would provide a template for defining an individual's AD stage and dictating stage-dependent therapeutic strategies, especially with regard to facilitating secondary prevention of AD. Therefore, identifying the temporal ordering sequence ("TOS") of AD biomarkers is essential in uncovering AD development processes and designing effective treatment strategies.

After decades of research, our knowledge of the nature of AD development has extended from a single pathway to a complex system. An earlier concept recognized β-amyloid ("Aβ") deposition as the earliest trigger, causing downstream neurodegeneration and cognitive deficit in turn. However, this linear pathway concept appears to be flawed given that Aβ removal has proven ineffective in improving clinical outcomes.

Recent studies indicate several neurodegenerative biomarkers arise upstream in AD. Specifically, neural dysfunction would induce Aβ pathologies, and the induced soluble Aβ peptides can further exacerbate neural dysfunction before fibrillary Aβ deposits; this corroborates observations of aberrant hippocampal hyperactivity and default mode network ("DMN") hypoconnectivity or hypometabolism in apolipoprotein E ("APOE") ε4 carriers without detectable Aβ deposition. Tau pathology also is required in mediating Aβ toxicity. These diverse pathophysiological events constitute a temporal-dependent process underlying AD development.

Three major technical challenges impede the determination of the optimal TOS among AD biomarkers. First, the traditional symptom-based group definition involves biologically heterogeneous populations and, therefore, poses a great challenge for disease staging. Second, the dichotomizations of biomarker values by "cut-off" thresholds appear to deviate from the continuous nature of AD progression. Also, the cut-points are difficult to standardize across laboratories since disease onset is insidious. Third, the optimal TOS determination among multiple biomarkers generally requires a large cohort with a long follow-up period to link preclinical to advanced AD stages, complicating study design and significantly raising costs.

Thus, there remains a need to provide systems and methods for determining the optimal TOS of pathophysiological events in AD, represented by corresponding dynamic biomarkers, in order to accurately stage an individual across the whole AD spectrum.

SUMMARY OF THE DISCLOSURE

The present disclosure addresses the aforementioned drawbacks by providing a computer-implemented method for generating a quantitative index value representative of an Alzheimer's disease stage. Biomarker data obtained from a subject are provided to a computer system, as is an optimal biomarker event sequence representative of a temporally ordered sequence of biomarker events associated with Alzheimer's disease. In some embodiments, the optimal biomarker event sequence is provided to the computer system by determining the optimal biomarker event sequence based on the biomarker data. A subject-specific risk index value is computed by the computer system using the optimal biomarker event sequence and the biomarker data. A report based on the subject-specific risk index value is then generated, wherein the report quantitatively characterizes Alzheimer's disease risk events for the subject.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

In FIG. 6A, the y-axis shows the $S_{optimal}$ and the x-axis shows the CARE index value at which the corresponding event occurred. In FIG. 6B, bootstrap cross-validation of $S_{optimal}$ is illustrated. Each entry in the matrix represents the proportion of $S_{optimla}$ during 500 bootstrap samples. The proportion values range from 0 to 1 and correspond to the color, from white to black.

In FIG. 8A, the proportion of EMCI (yellow) and LMCI (red) subjects at each CARE index value was plotted together with the CN (cyan) and AD (black) subjects, indicating heterogeneous CARE index distributions within groups. In FIG. 8B, a box plot of the CARE index value differences between groups. The median CARE index value for CN, EMCI, LMCI, and AD groups are 2, 4, 6, and 9, respectively. The two-sample t-tests between CN and EMCI, CN and LMCI, EMCI and LMCI, AD and LMCI showed significant differences. The red "O" denotes an outlier in the CN group.

FIG. 19A shows the number of patients in each diagnostic category at each individual CARE index stage at baseline from the ADNI dataset. Each CARE index stage on the x-axis corresponds to the occurrence of a new biomarker transition event. Score 0 corresponds to no events having occurred and stage 10 is when all events have occurred. FIG. 19B shows a boxplot representing the distribution comparison of N-MCI and P-MCI. For each boxplot, the band represents the median value, the box represents the interquartile range, and whiskers show the range of data without outliers (an outlier being defined as any value that lies more than one and a half times the interquartile range from either end of the box). Differences were assessed between the two groups using Mann-Whitney tests; ***p<0.001. FIG. 19C shows the power of receiver operating characteristic (ROC) curve of the CARE index 'classifier' in classifying the diagnosis of P-MCI versus N-MCI at baseline in the ADNI dataset. The numbers next to ROC curve indicate CARE index threshold.

FIG. 20A shows the number of patients in each diagnostic category at each individual CARE index stage at baseline from the NADS dataset. FIG. 20B shows a boxplot representing the distribution comparison of N-MCI and P-MCI. For each boxplot, the band represents the median value, the box represents the interquartile range, and whiskers show the range of data without outliers (an outlier being defined as any value that lies more than one and a half times the interquartile range from either end of the box). Differences were assessed between the two groups using Mann-Whitney tests; ***p<0.001. FIG. 20C shows power of ROC curve of the CARE index 'classifier' in predicting the P-MCI versus N-MCI at baseline in the NADS dataset. The numbers next to ROC curve indicate CARE index threshold.

FIGS. 21A-21C represent comparisons of the power of ROC curve of CARE index and individual behavioral, gray matter, and functional indices in the ADNI dataset, respectively. FIGS. 21D-21F represent comparisons of the power of ROC curve of CARE index and individual behavioral, gray matter, and functional indices in the NADS dataset, respectively.

FIG. 23A shows the optimal temporal sequence, $S^{optimal}$, of the 10 biomarkers to calibrate the CARE index. The y-axis shows the sequence and the x-axis shows the corresponding CARE index score. Each entry in the matrix represents the proportion of the $S^{optimal}$ calculated from the 500 bootstrap samples. The proportion values range from 0 to 1 and correspond to the color bar. The $S^{optimal}$s with their corresponding biomarkers are 1, increased HIP FCI; 2, decreased PCC FCI; 3, decreased Aβ concentration; 4, increased p-tau concentration; 5, decreased MMSE score; 6, increased ADAS score; 7, decreased HIP GMI; 8, decreased AVLT score; 9, decreased FUS GMI; 10, increased FUS FCI. FIG. 23B shows the distributions of the CARE index score in each group. FIG. 23C shows that the CARE index score showed gradual increases from the CN to MCI to Alzheimer's disease groups. The median CARE index scores of the CN, MCI, and Alzheimer's disease groups were two, five, and nine, respectively. FIG. 23D shows the CARE index score for the ε4 carriers and non-carriers within each group. The ε4 carriers showed a significantly higher CARE index score than the non-carriers in the MCI group.

DETAILED DESCRIPTION

Described here are systems and methods for computing a quantitative index that characterizes Alzheimer's disease ("AD") risk events based on a temporally ordered sequence of biomarker events. In general, the systems and methods described here implement a modified event-based probabilistic ("EBP") model to calculate the risk index. The systems and methods described here are capable of providing early detection of preclinical AD developmental events (e.g., before the detectability of β-amyloid protein and phosphorylated tau proteins).

The conceptual frameworks of the EBP model were initially developed and applied to study seriation in determining the temporal ordering of fossil occurrence in paleontology. The EBP model does not make any a priori assumptions about the sequence in which biomarker events occur, except that the sequence is consistent for all subjects. Rather, the EBP model estimates the probability of the event sequences using real-world data.

In an EBP model, for a set of N events, $\{E_1, E_2, \ldots, E_N\}$, measured by N biomarkers, $\{x_1, x_2, \ldots, x_N\}$, the temporal ordering sequence of events, $S=\{s(1), s(2), \ldots, s(N)\}$, is calculated by a permutation of the integers $1, \ldots, N$. For subjects $j=1, \ldots, J$, the dataset X can be regarded as $X=\{X_1, X_2, \ldots, X_J\}$. Specifically, data for the $j^{th}$ subject is given by $X_j=\{x_{1j}, x_{2j}, \ldots, x_{Nj}\}$, where $x_{ij}$ is $i^{th}$ biomarker measurement for the $j^{th}$ subject.

The systems and methods described here include determining the optimal temporal ordering sequence of biomarker events in a data-driven manner, based on the criteria that the optimal temporal ordering sequence, $S_{optimal}$, yields the highest probability in measuring a dataset, X (i.e., the $p(X|S)$ value of $S_{optimal}$ calculated to be maximal among all of the possible sequences). As will be described below, the optimal sequence, $S_{optimal}$, can then be used as a basis for calculating a risk index for assessing AD.

Figure 1:
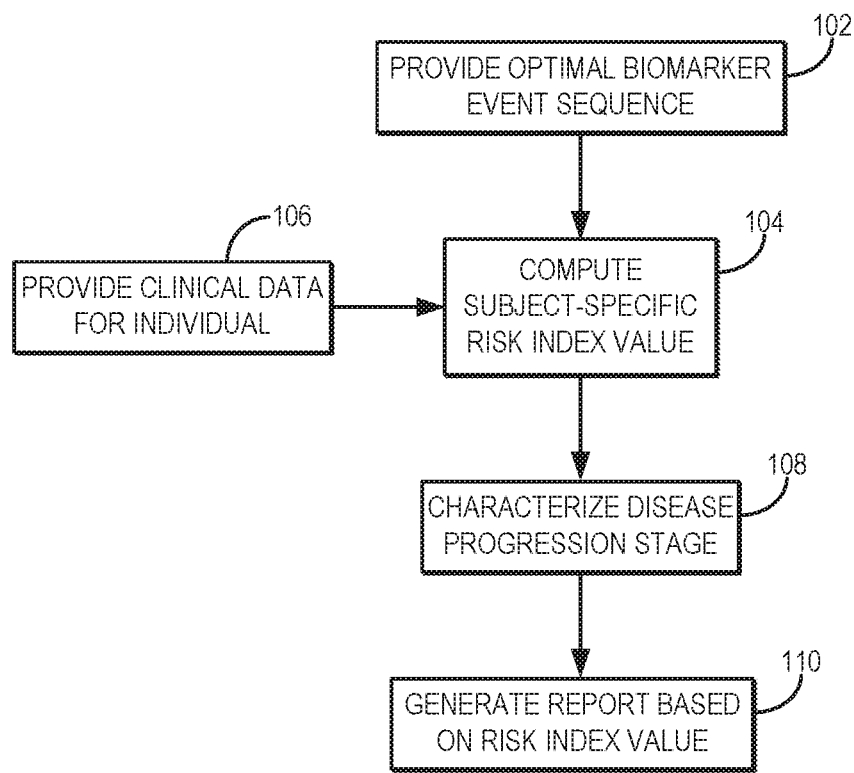
FIG. 1 is a flowchart setting forth the steps of an example method for computing a risk index for numerically characterizing AD risk events.

Referring now to FIG. 1, a flowchart is illustrated as setting forth the steps of an example method for computing a risk index for numerically characterizing AD risk events. This risk index can thus be referred to as a "CARE" (characterizing AD risk events) index.

The method includes providing an optimal sequence of biomarker events to a computer system, as indicated at step 102. The optimal sequence, $S_{optimal}$ can be provided by retrieving a previously determined sequence from data storage, or by determining an optimal sequence based on available biomarker data. An example of determining an optimal sequence of biomarker events is described below with reference to FIG. 2. Biomarker data that can be associated with the optimal sequence, $S_{optimal}$, can include a combination of functional, molecular, cognitive, or clinical biomarkers. As one example, biomarker data can include images or data acquired using resting-state functional MRI, diffusion-weighted MRI, or arterial spin labeling MRI. As another example, biomarker data can include metrics computed from such images or data, including functional connectivity indices, gray matter indices, or cerebral blood flow indices. Biomarker data can also include cerebrospinal fluid biomarkers, such as β-amyloid protein and phosphorylated tau protein concentrations, and can also include cognitive test scores.

Referring still to FIG. 1, a subject-specific risk index is then computed based on the optimal sequence of biomarker events, as indicated at step 104. Clinical data related to the subject is provided in step 106 and used, in part, to determine the subject-specific risk index. As an example, to determine a particular subject's AD risk stage, the likelihood value of each possible sequential order number, k, can be calculated. The individual AD stage at which the order number, k, with the highest likelihood value in the optimal sequence, $S_{optimal}$, can then be computed as, $$\arg\max_k p(k) = \prod_{i=1}^{k} p\left(x_{ij} \mid E_{S_{optimal}(i)}\right) \prod_{i=k+1}^{N} p\left(x_{ij} \mid \neg E_{S_{optimal}(i)}\right). \quad (1)$$

The $S_{optimal}$ order reflects sequential pathophysiological events, corresponds to the sequential event occurrence from one to the next, and provides a numerical score to measure disease progression from one stage to the next. In some embodiments, a K-means algorithm can be implemented to stabilize the distribution of event-occurrence and non-occurrence.

In some embodiments, the CARE index can be used in statistical analyses to associate particular CARE index values with a clinical stage. In these embodiments, the clinical data for the subject can be used together with the subject-specific CARE index to characterize a disease progression stage for that subject, as indicated at step 108. As an example, the clinical data can include demographic information; clinically defined AD stages, including cognitively normal ("CN"), early mild cognitive impairment ("EMCI"), late mild cognitive impairment ("LMCI") and Alzheimer's disease ("AD"); and clinical scores, such as mini-mental state examination ("MMSE") scores. A report can then be generated using the calculated CARE index value, as indicated at step 110. As one example, the report can include displaying textual or visual information to a clinician, where that textual or visual information is based at least in part on the CARE index. The characterization of the subject's disease progression can also be provided in the generated report.

As one example, characterizing the subject's disease progression can include using one or more linear regression models to assess the relationship between the CARE index values and the corresponding MMSE scores, As another example, a nonlinear exponential model can be used, such as, $$CARE = b_0 + A(e^{-k(30-MMSE)}) \quad (2)$$

where the unknown parameters ($b_0$, A, and k) can be estimated using a nonlinear least squares algorithm. The maximum MMSE score is 30.

Figure 2:
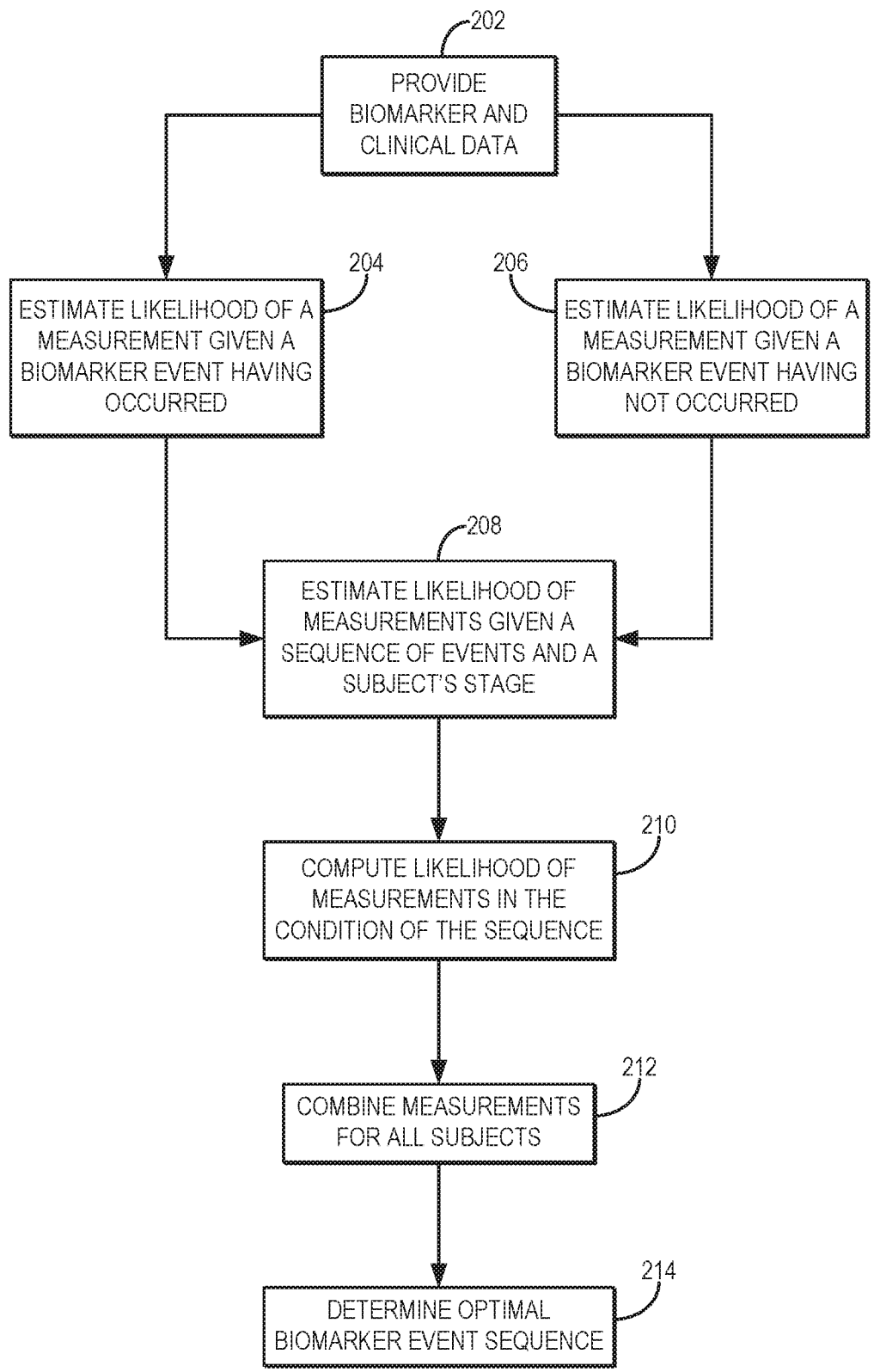
FIG. 2 is a flowchart setting forth the steps of an example method for determining an optimal sequence of biomarker events.

Referring now to FIG. 2, a flowchart is illustrated as setting forth the steps of an example method for determining an optimal sequence of biomarker events. The temporal optimized sequence of biomarker events links the appearance of any specific biomarkers in asymptomatic individuals to the subsequent emergence of clinical symptomatology across the whole spectrum of the AD development process, and thus is useful for characterizing a subject's clinical stage, such as by identifying subtypes of AD development processes.

The method includes providing biomarker data to a computer system, as indicated at step 202. In general, the biomarkers can include a combination of functional, molecular, cognitive, or clinical biomarkers. As an example, biomarker data can include functional connectivity indices; gray matter indices; cerebrospinal fluid biomarkers, such as $A\beta_{1-42}$ and p-tau concentrations; and cognitive test scores. In addition, clinical data sets from a suitable database of clinical data relevant to Alzheimer's disease are provided to the computer system, as indicated at step 204. Examples of such clinical data can include the following types of data obtained from a population: demographic information; clinically defined AD stages, including CN, EMCI, LMCI, and AD; and clinical scores, such as MMSE scores.

Based on the biomarker and clinical data, a likelihood of a measurement, $x_{ij}$, given a biomarker event, $E_i$, having occurred is estimated, as indicated at step 204. As one example, it can be hypothesized that ten events, represented by the ten example biomarkers listed above, can occur along with AD progression. This likelihood value can be estimated as, $$p(x_{ij}|E_i) \quad (3).$$

Similarly, a likelihood of a measurement, $x_{ij}$, given a biomarker event, $E_i$, having not yet occurred is estimated, as indicated at step 206. This likelihood value can be estimated as, $$p(x_{ij}|\neg E_i) \quad (4).$$

Using these estimated likelihoods, the likelihood of measurements, $X_j$, given a sequence of events, S, and a particular stage, k, is estimated, as indicated at step 208. This likelihood value can be estimated as, $$p(X_j \mid S, k) = \prod_{i=1}^{k} p(x_{ij} \mid E_{s(i)}) \prod_{i=k+1}^{N} p(x_{ij} \mid \neg E_{s(i)}). \quad (5)$$

In Eqn. (5), it is assumed that the $j^{th}$ subject is at stage, k. This means that for the $j^{th}$ subject, events $E_{s(1)}$, $E_{s(2)}$, ..., $E_{s(k)}$ have already occurred, and events $E_{s(k+1)}$, $E_{s(k+2)}$, ..., $E_{s(N)}$ have not yet occurred. Thus, in Eqn. (5), $$\prod_{i=1}^{k} p(x_{ij} \mid E_{s(i)}); \quad (6)$$

represents the overall likelihood of measurements given that corresponding events have already occurred, and $$\prod_{i=k+1}^{N} p(x_{ij} \mid \neg E_{s(i)}); \quad (7)$$

is the overall likelihood of measurements given that events have not yet occurred. The likelihood of measurements, $X_j$, in the condition of the sequence, S, is then computed, as indicated at step 210. This likelihood value can be computed by summing the likelihood values of measurements, $X_j$, across all possible stages, k, within a sequence, S, as follows, $$p(X_j \mid S) = \sum_{k=0}^{N} p(k) p(X_j \mid S, k). \quad (8)$$

The measurements for all subjects are then combined, as indicated at step 212. As a result of this combination, the probability of measurements given a particular sequence is computed as, $$p(X \mid S) = \prod_{j=1}^{J} p(X_j \mid S) = \prod_{j=1}^{J} \prod_{k=0}^{N} p(k) p(X_j \mid S, k) \quad (9)$$

-continued $$= \prod_{j=1}^{J}\prod_{k=0}^{N}p(k)\left(\prod_{i=1}^{k}p(x_{ij}\mid E_{s(i)}), \prod_{i=k+1}^{N}p(x_{ij}\mid \neg E_{s(i)})\right);$$

where it is assumed in Eqn. (9) that the intersubject relationships are independent. Based on the probability in Eqn. (9), computed for a number of different sequences, an optimal sequence of biomarker events can be determined, as indicated at step 214. In theory, the above analysis would need to be repeated for each possible sequence to determine the sequence, $S_{optimal}$, with the maximal value of $p(X|S)$. However, such a computation strategy is extremely time consuming. For example, the total calculation times would be 2.7942e+009, for 10 biomarker events, 11 possible stages (including stage 0), and 70 subjects. Therefore, an optimization algorithm can be used to improve processing efficiency.

In some embodiments, the likelihood described in Eqn. (5) can be normalized to define a normalized likelihood, $$p_{norm}(X_j|S,k) = A_j \cdot p(X_j|S,k) \tag{10};$$

where the normalization factor, $A_j$, is determined by, $$\sum_{k=0}^{N}P_{norm}(X_j\mid S,k) = A_j \cdot \sum_{k=0}^{N}p(X_j\mid S,k) = 1. \tag{11}$$

Using the normalized likelihood, the weighted average ("WA") stage, $k_{j,WA}$, for a subject, j, can be defined as, $$k_{j,WA} = \sum_{k=0}^{N}k \cdot P_{norm}(X_j\mid S,k). \tag{12}$$

In the method described above with respect to FIG. 2, the stage, k, that has the highest likelihood value determines an individual subject's disease stage. However, in some instances there may be missing biomarker data for that individual subject, which will pose a potential problem. For example, when a subject's disease stage corresponds to the missing biomarker, it may not be possible to determine the subject's disease stage in this "winner take all" approach. Rather, the disease stage will fall to the next available highest likelihood stage, most likely k−1 or k+1. To address this problem, the weighted average stage defined above in Eqn. (12) can be implemented. The weighted average stage of a subject can still be the same as k, even when the corresponding biomarker is missing.

Figure 3:
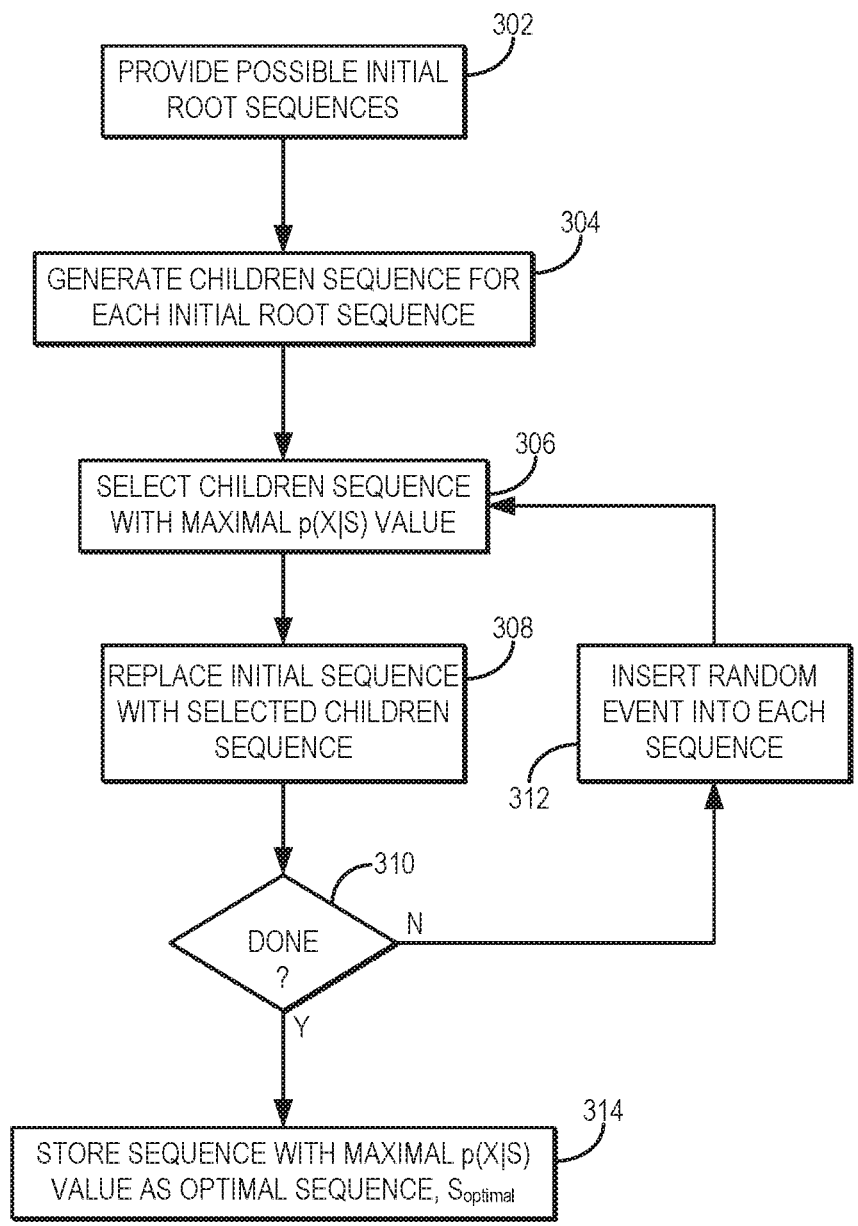
FIG. 3 is a flowchart setting forth the steps of an example method for determining an optimal sequence of biomarker events given a set of such sequences.

Referring now to FIG. 3, a flowchart is illustrated as setting forth the steps of an example method for determining an optimal sequence of biomarker events given a set of sequences. In this example, the method for determining the optimal sequence, $S_{optimal}$, is based on a self-growing greedy algorithm. It should be appreciated by those skilled in the art, however, that alternative methods for determining the optimal sequence from a set of sequences can also be implemented. The greedy algorithm explores the globally optimal solution by making the locally optimal choice at each stage, in a greedy heuristic manner. The greedy Markov chain Monte Carlo ("MCMC") algorithm is a useful approach to find the globally optimal results.

The amount of time such an analysis would take is unpredictable due to the randomized initial sequence, and it may be quite long due to the inevitable searching loop. Therefore, a modified greedy algorithm can instead be utilized to address this deficiency.

This example method includes providing a set of possible initial root sequences, as indicated at step 302. For instance, the initial root sequences can be provided by randomly selecting a number m<N of biomarker events from N total available biomarker events and assigning those events to a given sequence. As one example, there may be ten biomarker events to consider (i.e., N=10), and in this example two biomarker events can be selected in each initial root sequence (i.e., m=2). Children sequences are then generated for each initial root sequence, as indicated at step 304. As one example, each children sequence can be generated by inserting a randomly selected biomarker event from the remaining available events for a given initial root sequence.

The children sequence with the maximal $p(X|S)$ value is then selected, as indicated at step 306, and this selected children sequence replaces its corresponding initial root sequence, as indicated at step 308. A determination is then made at decision block 310 whether all N biomarker events have been used. If not, another random event is inserted into each children sequence, as indicated at step 312, and steps 306-310 are repeated until all available biomarker events have been accounted for. The sequence with the maximal $p(X|S)$ value is then stored as the optimal biomarker event sequence, $S_{optimal}$, as indicated at step 314.

Example 1

An example study was performed to evaluate the EBP model described above. The methods implemented in this study and the corresponding results are described below.

Example 1: Methods

Subject Data Collection. In this study, data from the Alzheimer's Disease Neuroimaging Initiative 2 ("ADNI 2") database was utilized. In brief, the experimental substudies in ADNI 2 include three different types of magnetic resonance image sequences: (1) resting-state functional connectivity magnetic resonance imaging (R-fMRI), (2) diffusion tensor imaging (DTI), and (3) arterial spin labeling cerebral blood flow (ASL-CBF) perfusion.

R-fMRI data was also downloaded from the Laboratory of Neuro Imaging (LONI). This data included 225 subjects with four groups of clinical diagnoses: cognitively normal (CN), early mild cognitive impairment (EMCI), late MCI (LMCI), and Alzheimer's Disease (AD), as well as an apolipoprotein E (APOE) genotype for each subject.

Of the 225 total subjects, 144 were selected from the ADNI 2 database based on the following requirements: (1) all subjects had at least one R-fMRI scan with corresponding anatomical scans; (2) all subjects had cerebrospinal fluid (CSF) β-amyloid (Aβ) and phosphorylated tau (p-tau) concentration values; (3) all subjects had scores on the Mini-Mental State Examination (MMSE), modified 13-item Alzheimer's Disease Assessment Scale-Cognitive Subscale (ADAS-Cog), and Rey Auditory Verbal Learning Test (AVLT) (immediate recall score, i.e., the sum of trials 1 to 5). Together, the 144 subjects included 45 CN, 42 EMCI, 32 LMCI, and 25 AD subjects. Note that 18 CN subjects were identified as significant memory concern subjects as they had subjective memory complaints but no objective cognitive impairment. Subject demographic information is detailed in Table 1.

TABLE 1

Demographic and clinical data for all subjects

|  | CN* (n = 45) | EMCI (n = 42) | LMCI (n = 32) | AD (n = 25) | F value | p value |
|---|---|---|---|---|---|---|
| Gender (M/F) | 20/25 | 19/22# | 20/12 | 13/12 | 0.98 | 0.40 |
| Age (Years) | 73.6 ± 6.4 | 71.5 ± 6.9 | 72.1 ± 8.1 | 73.9 ± 6.9 | 0.98 | 0.41 |
| Education (Years) | 16.3 ± 2.5 | 15.1 ± 2.4 | 16.8 ± 2.4 | 15.7 ± 2.8 | 2.93 | 0.04 |
| MMSE | 28.8 ± 1.3 | 28.0 ± 1.8 | 27.5 ± 1.9 | 22.6 ± 2.8 | 63.13 | $<7.0 \times 10^{-26}$ |
| ADAS-Cog | 5.4 ± 2.6 | 8.6 ± 3.4 | 11.4 ± 5.3 | 21.7 ± 7.3 | 71.36 | $<4.6 \times 10^{-28}$ |
| Aβ | 201.5 ± 54.2 | 177.1 ± 61.0 | 170.5 ± 48.2 | 141.0 ± 40.0 | 7.21 | $<2.0 \times 10^{-4}$ |
| p-tau | 32.7 ± 14.2 | 43.2 ± 24.0 | 44.4 ± 21.6 | 55.4 ± 26.9 | 6.21 | $<0.5 \times 10^{-3}$ |
| AVLT | 44.6 ± 10.4 | 37.3 ± 10.4 | 32.7 ± 7.6 | 22.6 ± 7.1 | 31.48 | $<1.3 \times 10^{-15}$ |

*including 18 significant memory concern subjects who were cognitively normal.

In Table 1, clinical data are expressed as mean±standard deviation. F-values and p-values were obtained by one-way analysis of variance. There were significant differences among the four groups for education years; scores of MMSE, ADAS-Cog, and AVLT; and CSF Aβ and p-tau levels.

Imaging Acquisition. Briefly, in the ADNI data acquisition process, R-fMRI datasets were scanned on 3.0 Tesla (T) MRI scanners. During the resting-state acquisitions, no specific cognitive tasks were performed, and the participants were instructed to relax with their eyes open inside the scanner. Axial R-fMRI images of the whole brain were obtained in seven minutes with a single-shot gradient echo planar imaging (EPI) sequence and the following parameters: repetition time (TR)=3 s, echo time (TE)=30 ms, flip angle=80°, slice number=48, gap=0, slice thickness=3.3 mm, matrix size=64×64, field of view=21×21 cm. High-resolution MPRAGE 3D sagittal images were acquired with the following parameters: TE/TR=3.16/6.8 ms, flip angle=9°, slice number=170, slice thickness=1.2 mm, matrix size=256×256.

Resting-State Image Preprocessing. Conventional preprocessing steps were conducted using Analysis of Functional NeuroImages (AFNI) software (http://afni.nimh.nih.gov/afni/), SPM8 (Wellcome Trust, London, United Kingdom), and MATLAB (Mathworks, Natick, Mass.). The preprocessing allows for T1-equilibration (removing the first 15 seconds of R-fMRI data); slice-acquisition-dependent time shift correction (3dTshift); motion correction (3dvolreg); detrending (3dDetrend); despiking (3dDespike); spatial normalization (original space to the Montreal Neurological Institute [MNI] space, SPM8); averaging white matter and CSF signal retrieval (3dROIstats) using standard SPM white matter and CSF mask in the MNI space; white matter, CSF signal, and motion effect removal (3dDeconvolve); global signal removal necessity check (the global signal will be removed if necessary);[16] and low-frequency band-pass filtering (3dFourier, 0.015-0.1 Hz).

Figure 4:
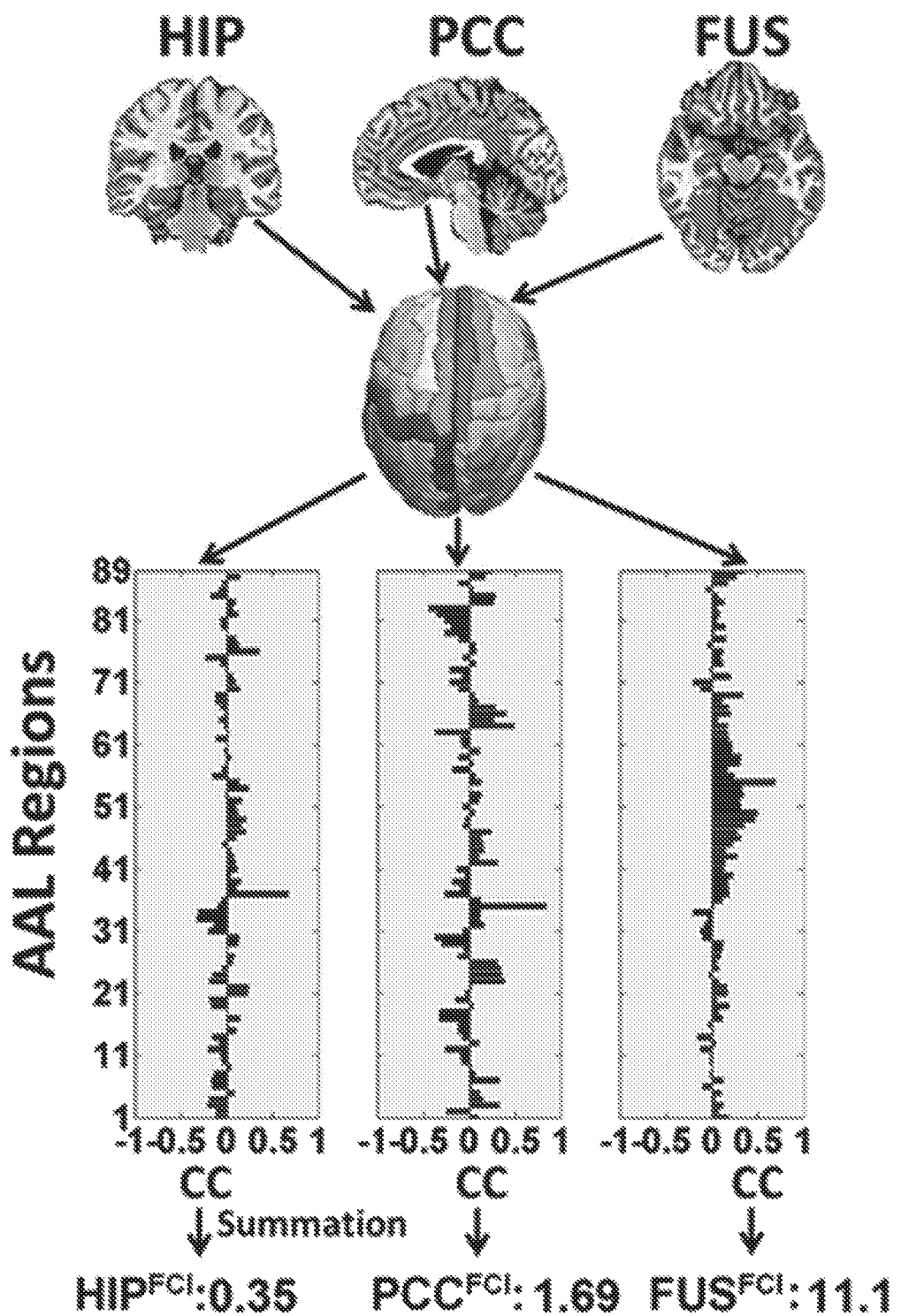
FIG. 4 depicts calculation of $HIP^{FCI}$, $PCC^{FCI}$, and $FUS^{FCI}$. First, the whole cerebral cortex was separated into 90 regions based on the AAL template, and the average BOLD time series for each region was extracted. Then, the functional connectivity strengths between bilateral HIP, PCC, or FUS and other brain regions were calculated using the Pearson cross-correlation analysis. Thus, a vector consisting of 89 CC values for each HIP, PCC, or FUS was obtained. Finally, the strengths of $HIP^{FCI}$, $PCC^{FCI}$, and $FUS^{FCI}$ were determined by summating 89 CC values within each vector.

Functional Connectivity Index of Regions of Interest. This study calculated the functional connectivity index (FCI) of three regions of interest (ROIs): bilateral hippocampus ($HIP^{FCI}$), posterior cingulate cortex ($PCC^{FCI}$), and fusiform gyrus ($FUS^{FCI}$). FIG. 4 depicts the FCI calculation stream. First, the whole cerebral cortex was separated into 90 regions based on the Automated Anatomical Labeling (AAL) template, and the blood oxygen level dependent (BOLD) time series of each region was extracted using the AAL template mask from the preprocessed resting-state dataset. Second, functional connectivity between each ROI and the other brain regions was calculated using the Pearson cross-correlation analysis. Thus, a vector containing 89 cross-correlation coefficient (CC) values for each ROI was obtained. Finally, each ROI's FCI value (identified separately as $HIP^{FCI}$, $PCC^{FCI}$, and $FUS^{FCI}$) was calculated by summating 89 CC values within each ROI's vector and averaging them across each pair of bilateral ROIs.

Gray Matter Index. For each individual, the gray matter index (GMI) of each brain region (using the same AAL template) was calculated using SPM8 software. First, the anatomical image of each individual's brain was normalized into the MNI space. Second, the gray matter of the whole brain was segmented and separated from white matter and CSF areas, and a threshold of 0.8 was used to exclude non-gray-matter areas. Third, each region's GMI was determined by the summation of gray matter concentration values of all voxels within the region and averaged across each pair of bilateral ROIs.

Events Set Assumption. In this study, it was hypothesized that 10 events, represented by 10 biomarkers, occur along with AD progression: (1) $HIP^{FCI}$ (hyperconnectivity is regarded as abnormal); (2) $PCC^{FCI}$ (hypoconnectivity is denoted as abnormal); (3) $FUS^{FCI}$ (hyperconnectivity is recognized as abnormal); (4) two GMI biomarkers (a lower GMI is defined as abnormal): $HIP^{GMI}$ and $FUS^{GMI}$; (5) two CSF biomarkers: $Aβ_{1-42}$ and p-tau concentration; (6) three cognitive biomarkers: MMSE, AVLT, and ADAS-Cog scores.

Event Occurring and Event Not Occurring Distribution Modeling. A mixture of two normal Gaussian distributions was used to fit the event data from the CN and AD groups, based on the assumption that an event occurring and an event not occurring are estimated by a mixed distribution of normal and disease groups. The fitted Gaussian distributions separated the data into two groups: abnormal (event occurred) and normal (event did not occur). A k-mean clustering algorithm was used to separate the whole distribution into two clusters before applying the Gaussian mixture model fitting. The rational for this implementation was that the randomly sampled algorithm of the direct Gaussian mixture model fitting may induce an inter-fitting variance in the obtained model. Estimating the events sequence with maximum likelihood would significantly confound the greedy algorithm (discussed above). Therefore, the k-mean clustering algorithm was used first and treated the mean and standard deviation of the two clusters as the initial state, instead of random samples, for the direct Gaussian mixture model fitting. This modified modeling method would lead to inter-fitting consistency in the obtained model.

Event-Based Probabilistic Model. The conceptual frameworks of the EBP model are described above in detail with respect to FIGS. 1-3. As described above, the EBP model does not make any a priori assumptions about the sequence in which biomarker events occur, except that the sequence is consistent for all subjects. Rather, the EBP model estimates the probability of the event sequences using real-world data.

Self-Growing Greedy Algorithm. In this study, the modified greedy algorithm described above with respect to FIG. 3 was implemented to determine optimal sequences, $S_{optimal}$. Specifically, a set of all possible initial root sequences, each of which contained two randomly selected events from the 10 biomarker events total, was initialized. Second, for each initial sequence, S, the children of S were generated by inserting a randomly selected event from the remaining events. Third, the children sequence with the maximal $p(X|S)$ value was selected and used to replace the initial sequence. Then, another randomly selected event was entered into the sequence, and the second and the third steps were repeated until no events were left. Thus, whole sequences were generated for each root sequence.

Ultimately, the sequence with the maximum $p(X|S)$ value was determined as the final optimal sequence, $S_{optimal}$. This greedy algorithm was repeated 100 times to ensure $S_{optimal}$ had a high reliability. This study used 45 CN and 25 AD subjects to determine $S_{optimal}$. Note that the EMCI and LMCI subjects were not used to train $S_{optimal}$. The $S_{optimal}$ order reflects sequential pathophysiological events, corresponds to the sequential event occurrence from one to the next, and provides a numeric score to measure disease progression from one stage to the next.

Individual Staging Based on the Obtained Sequence. To determine each subject's AD risk stage, the likelihood value of each possible sequential order number k was calculated and the individual AD stage at which the order number k with the highest likelihood value in the final sequence $S_{optimal}$ was defined using Eqn. (1). In Eqn. (1), implications of $$\prod_{i=1}^{k} p(x_{ij} | E_{S_{optimal(i)}}) \text{ and } \prod_{i=k+1}^{N} p(x_{ij} | \neg E_{S_{optimal(i)}})$$

refer to those in Eqn. (5), except that the optimal sequence, $S_{optimal}$, is obtained.

CARE Index. The EBP model-based stage, k, from Eqn. (1) is the order number of biomarker events with the highest likelihood value in $S_{optimal}$. To avoid possible confusion between clinically defined AD stages (e.g., EMCI, LMCI, and AD) and biomarker-event-based stages, the latter is defined as the index for numerically characterizing AD risk events (CARE), or the CARE index.

Statistical Analysis. The one-way analysis of variance (ANOVA) was used to compare demographic information and clinical data among the four clinically defined groups (45 CN, 42 EMCI, 32 LMCI, and 25 AD) comprising 144 subjects. Then, ANOVA was applied to detect differences in CARE index among the four groups. The sources of the among-group differences were further identified by post-hoc random-effect two-sample t tests. (For ANOVA, the statistical significance level was set at $p<0.05$; for post-hoc t tests, the statistical significance level was set at Tukey-Kramer corrected $p<0.05$.)

Multiple linear regression models were employed to study the relationship between the CARE index values and the corresponding MMSE score obtained from the four groups, as follows:

CARE Index$(s)=b0+b1 \cdot I(s,\text{EMCI})+b2 \cdot I(s,\text{LMCI})+$
$b3 \cdot I(s,\text{AD})+b4 \cdot \text{MMSE}(s)+b5 \cdot \text{MMSE}(s) \cdot I(s,$
$\text{EMCI})+b6 \cdot \text{MMSE}(s) \cdot I(s,\text{LMCI})+b7 \cdot \text{MMSE}(s) \cdot$
$I(s,\text{AD})+\varepsilon(s)$ where s is subject variable, the group indicator variable I(s,EMCI) equals one if subjects is within the EMCI group, 0 otherwise, etc. This model allows the simultaneous fitting of four regression lines to the data and corrects for errors due to the multiple group effect.

A nonlinear exponential model was also employed to fit to all of the data:

CARE index$(s)=b0+A \cdot (1-e^{-k(30-\text{MMSE}(s))})$

The unknown parameters (b0, A, k) in the above model were estimated using a nonlinear least squares algorithm. The maximum score of MMSE is 30.

Figure 5:
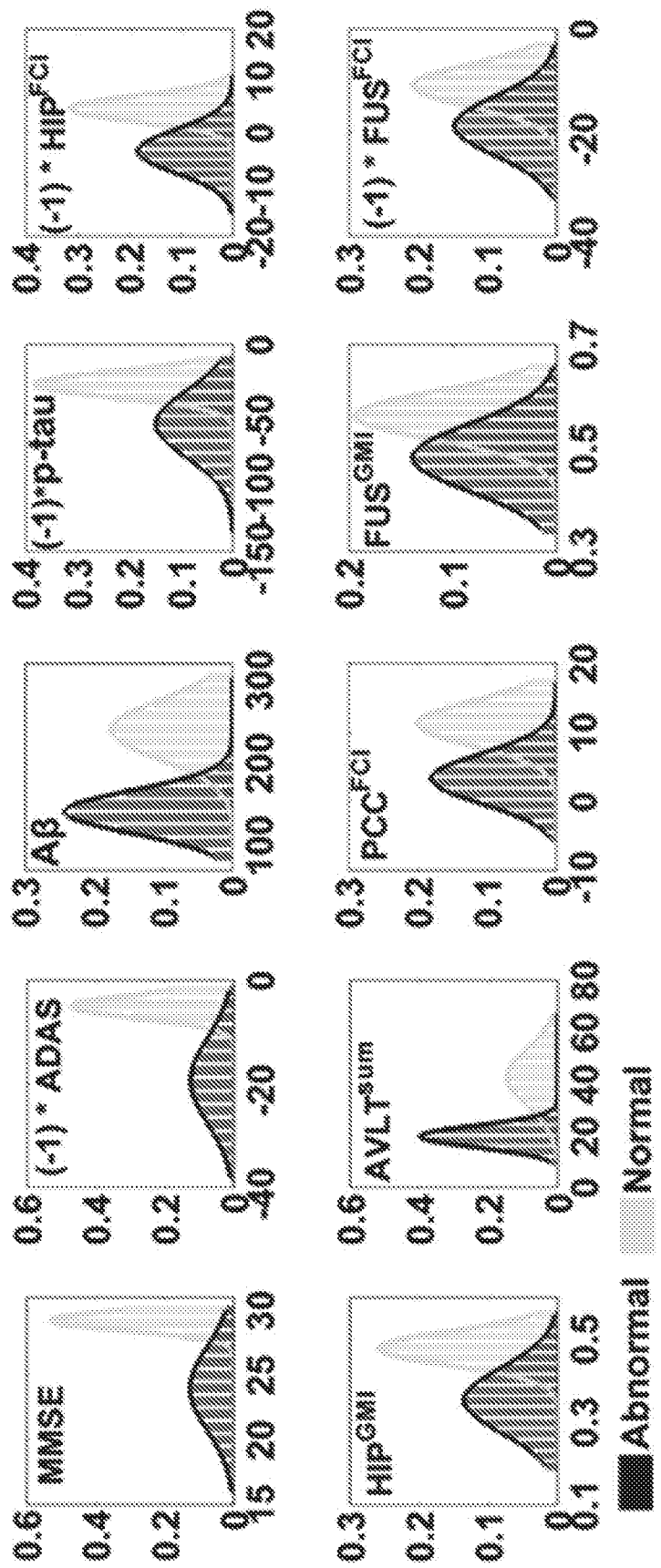
FIG. 5 depicts probability distributions of event abnormal (occurring) and normal (not occurring) measured by biomarkers from the AD (black) and CN (cyan) populations in an example study. The y-axis denotes the proportion of subjects, while the x-axis indicates the detected value of each biomarker measurement. The (−1) is employed to reverse the signs of the biomarker, indicating the left distribution is an event that occurred and the right distribution is an event that did not occur.
Figure 12:
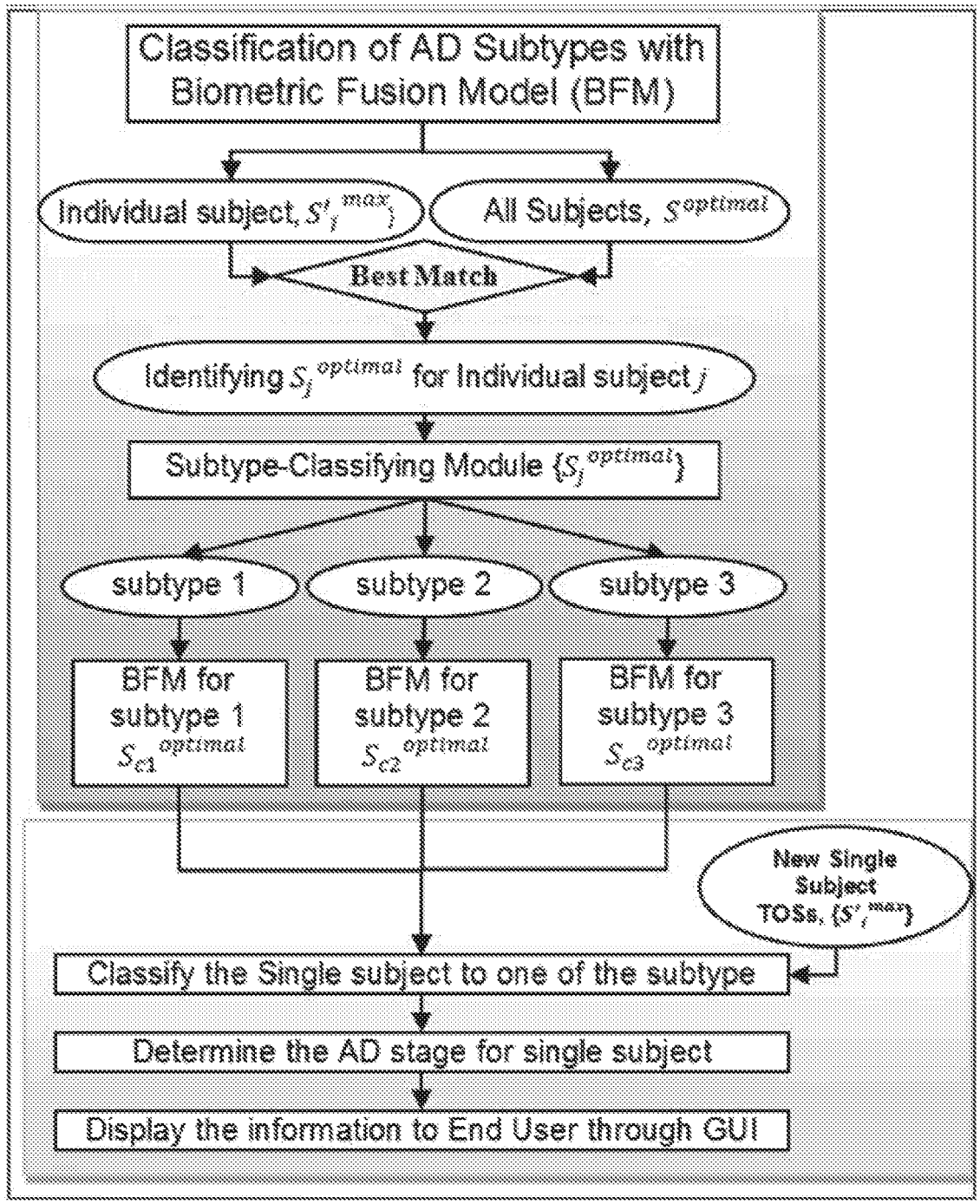
FIG. 12 is a flowchart setting forth the steps of an example method for implementing AD subtype classification based on optimal temporal ordering sequences of biomarker events, which can be determined using the algorithms described herein.

Classifying the subtypes of AD disease pathways. Specific procedures for AD subtype classification are summarized in FIG. 12. The first step is to determine the temporal ordering sequence for each subject by estimating the maximum likelihood of Eqn. (2). For each single subject, j, the probabilities $p(x_{ij}|E_i)$ and $p(x_{ij}|\neg E_i)$ can be obtained from the normal and abnormal group distributions of each biomarker, i, as shown in FIG. 5. For a specific subject, j, to satisfy the maximum value of $p(X_j|S^*, k)$, there could be a set of temporal ordering sequences, $\{S_j^{max}\}$, that achieves this result because the probability of events occurring or not occurring can be combined freely due to the commutative principle of multiplication.

To estimate an optimal temporal ordering sequence, denoted as $S_j^{optimal}$, for an individual among $\{S_j^{max}\}$, a supervised algorithm was implemented to obtain the $S_j^{optimal}$ that is maximally matched with the generalized optimal temporal ordering sequence, $S^{optimal}$. As described above, $S^{optimal}=\{s_1, s_2, \ldots s_i, s_N\}$ is an optimal set of sequential biomarker events, where $s_i$ refers to a specific biomarker event, i, in $S^{optimal}$. Letting $\{S_j^{max}\}=\{S_j^{max_1}, S_j^{max_2}, \ldots, S_j^{max_K} \ldots \}$, and $S_j^{maax_k}=\{s'_1, s'_2, \ldots s'_i, s'_N\}$, and $s'_i$ the biomarker event in $s_j^{max_k}$, to determine the $S_j^{optimal}$ the sequence $S_j^{max_k}$ that has the minimum Euclidean distance is selected. The minimum Euclidean distance ("ED") can be described as, $$\text{argmin}_{S_j^{max_k}}(\text{ED}(S_j^{max_k}))=\sqrt[2]{\sum_i^N (s'_i-s_i)^2} \quad (13).$$

If $S_j^{max_k}$ is unique, then this $S_j^{max_k}$ is the individual's $S_j^{optimal}$; otherwise, within the set of $\{S_j^{max_k}\}$, the $S_j^{optimal}$ that has highest consistency of the order (CO) compared with the $S^{optimal}$ sequence can be selected. To do this, the following is calculated:

$$\text{argmin}_{S_j^{max_k}}(\text{CO}(S_j^{max_k}))=\sqrt[2]{\sum_{i+1}^N ((s'_i-s'_{i-1})-(s_i-s_{i-1}))^2} \quad (14);$$

to obtain a unique $S_j^{optimal}$.

After obtaining the $S_j^{optimal}$ for each individual subject, a clustering analysis is conducted by comparing the cross correlation coefficient between each pair of individual $S_j^{optimal}$ using hierarchical clustering methods. The number of clusters can be determined according to a given hypothesis. Previous studies suggested that beside the typical AD pathways, which refers to the Amyloid cascade sequence, there are about 25% AD patients that showed the SNAP sequence. These two AD pathways, plus normal aging pathways, may account for three major clusters among the population. Therefore, in some embodiments, three clusters can be initially selected for analysis. With the obtained memberships of subjects in each cluster, a biometric fusion model ("BFM") can be applied within the cluster members to estimate the $S_{c1}^{optimal}$, $S_{c2}^{optimal}$, $S_{c3}^{optimal}$, respectively.

Methods for single subject subtype classification and stage determination. After the clustering analysis and obtained the individual cluster level $S_{ci}^{optimal}$, the next step is highly related to the clinical end-user: classification of an individual subject in different disease subtypes and determination of specific stage in the subtype. Specifically, a set of $\{S_j^{max}\}$ for the unclassified individual subject j, is first obtained and then the subtype of subject j is classified by comparing $S_j^{max_k}$ with $S_{c1}^{optimal}$, $S_{c2}^{optimal}$, $S_{c3}^{optimal}$ to determine the minimum Euclidean distance. If $S_j^{max_k}$ is unique, then this $S_j^{max_k}$ is the individual $S_j^{optimal}$. Otherwise, within the set of $\{S_j^{max_k}\}$ the $S_j^{optimal}$ that have highest consistence of sequence order compared with the subtype sequence of $S_{c1}^{optimal}$, $S_{c2}^{optimal}$, $S_{c3}^{optimal}$ can further be selected. The $S_j^{optimal}$ will thus have the maximum similarity with one of $S_{c1}^{optimal}$, $S_{c2}^{optimal}$, $S_{c3}^{optimal}$. After the individual is classified to a specific subtype, the stage, k, for the subject j that maximizes the value of $(X_j|S_{ci}^{optimal}, k)$ can be determined using the determined subgroup's $S_{ci}^{optimal}$.

Example 1: Results

Subject Information. As shown in Table 1, the four groups had no significant difference in demographic information except education years (F=2.93, p=0.04). By contrast, the MMSE, ADAS-Cog, and AVLT scores, as well as the CSF Aβ and p-tau levels, exhibited significant differences among groups.

Biomarker Events Distribution. In all 10 plotted event distributions (FIG. 5), distributions with lower values were recognized as abnormal (event occurred) and distributions with higher values as normal (event did not occur). Therefore, the values of biomarkers that defined a higher value as abnormal in nature, including the ADAS-Cog score, p-tau level, $HIP^{FCI}$, and $FUS^{FCI}$, were multiplied by (−1).

Figures 6A, 6B:
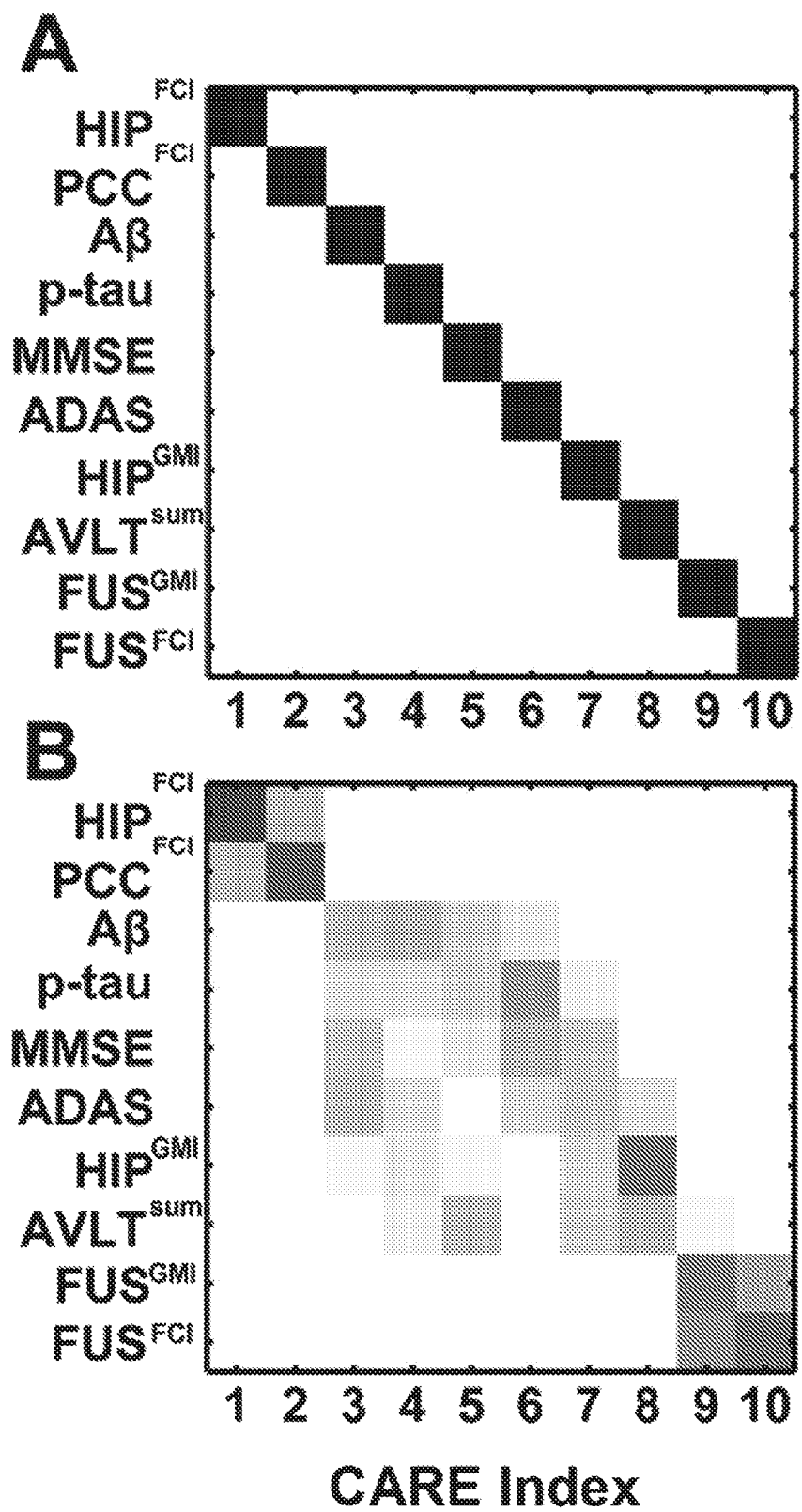
FIGS. 6A-6B depict optimal temporal ordering sequence, $S_{optimal}$, of the 10 AD Biomarkers estimated by the EBP model in an example study.

$S_{optimal}$ of Events. The $S_{optimal}$ represented by the 10 biomarkers was obtained and is presented in FIG. 6A. The first two disease events are represented by two functional biomarkers: increased $HIP^{FCI}$ and decreased $PCC^{FCI}$. The next two are CSF markers: decreased $A\beta_{1-42}$ and increased p-tau. The subsequent events are a mix of cognitive biomarkers (decreased MMSE, ADAS-Cog, and AVLT scores), as well as the gray matter structure biomarkers (decreased $HIP^{GMI}$ and $FUS^{GMI}$). The last event is increased $FUS^{FCI}$. Note that the optimal sequence of biomarker events (i.e., $S_{optimal}$), calculated from the CN and AD groups, was obtained and is reflected by a perfect diagonal pattern in the matrix (FIG. 6A). This result was obtained from application of the modified k-mean Gaussian mixture model fitting and the greedy algorithm described above, and, thus, event uncertainty was minimized.

To cross-validate the obtained $S_{optimal}$, the bootstrap approach was performed, in which the data were resampled 500 times to re-estimate the distributions of each event. The sequence probability of each event was estimated by the bootstrap samples (FIG. 6B). Event uncertainty primarily existed within three distinguished event clusters: (1) the early event cluster, including $HIP^{FCI}$ and $PCC^{FCI}$; (2) the middle event cluster, including CSF biomarkers, cognitive performance, and $HIP^{GMI}$; and (3) the later event cluster, including $FUS^{FCI}$ and $FUS^{GMI}$. Note that there is barely uncertainty among these three event clusters.

Figure 7:
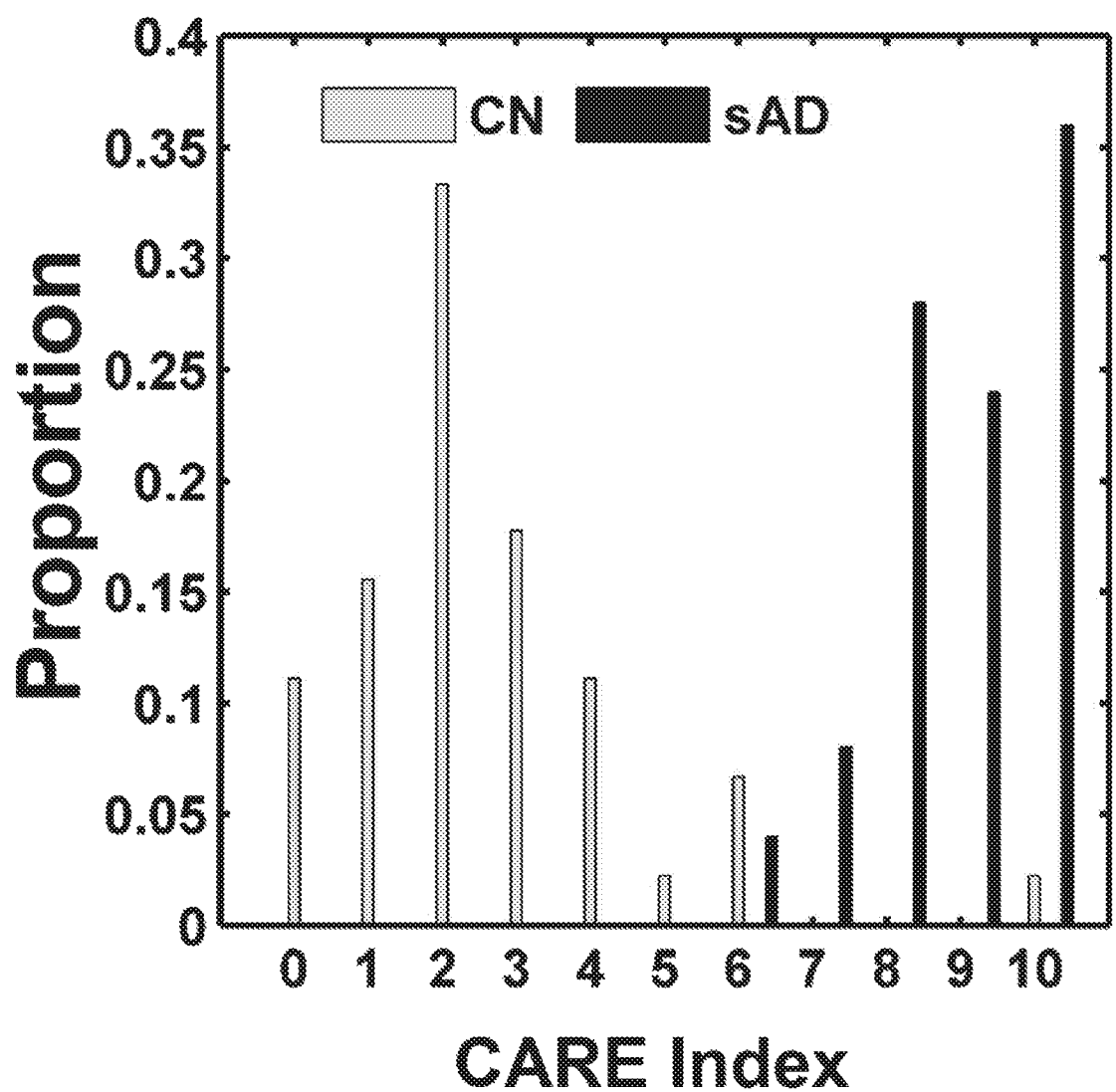
FIG. 7 depicts CARE index distribution of CN and AD groups of individual subjects calculated from the EBP model in an example study. The CARE index is ordered by the maximum likelihood event sequence. Each CARE index value corresponds to the occurrence of a biomarker event. CARE index value 0 corresponds to no events having occurred and CARE index value 10 corresponds to all events having occurred. Both CN and AD groups showed heterogeneous index distributions.
Figures 8A, 8B:
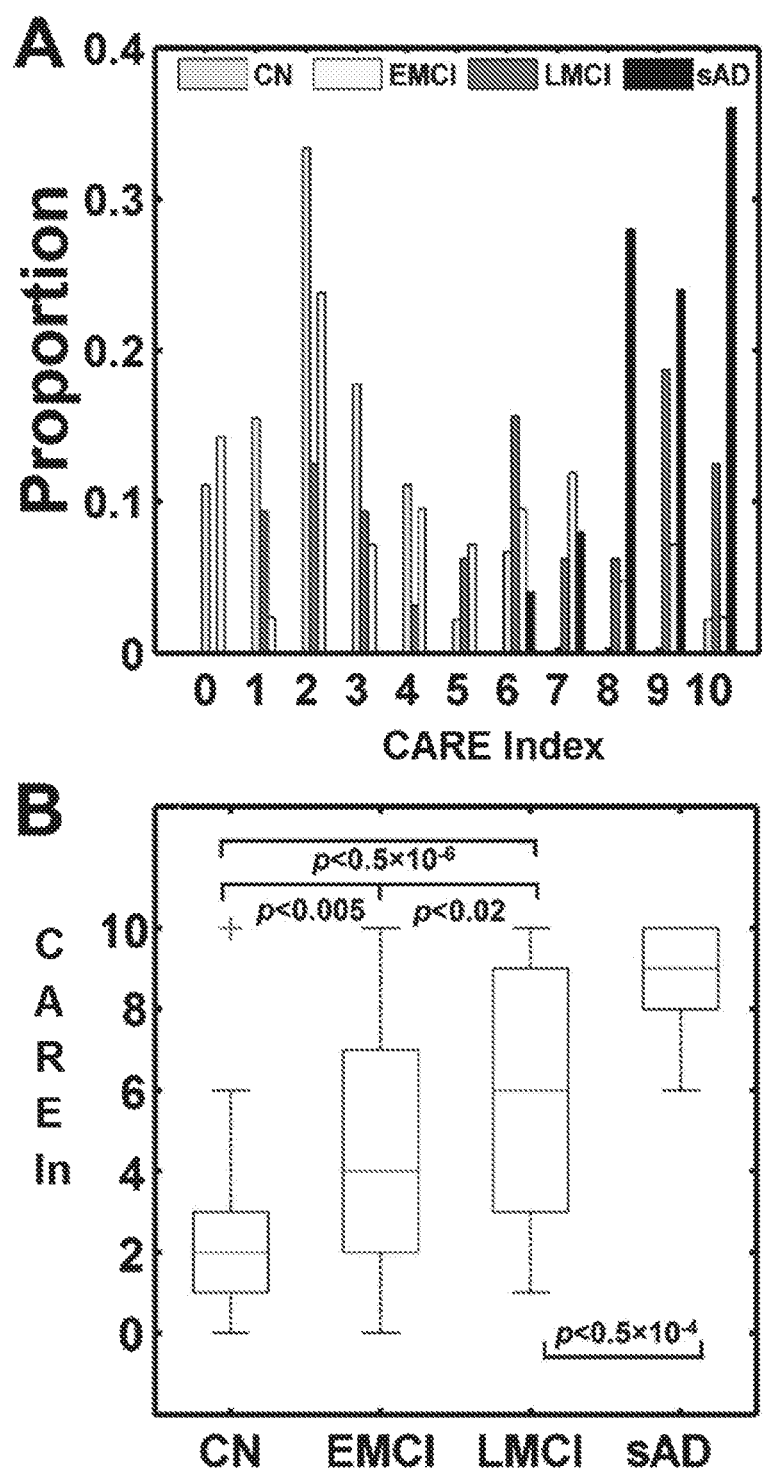
FIGS. 8A-8B depict heterogeneous care index distributions among CN, EMCI, LMCI, and AD groups in an example study.

Association of the CARE Index with Clinical stages. Using the EBP model-based biomarker events ordering, a CARE index value was obtained for each subject, regardless of the subject's clinical stage. Then, individual CARE index values were associated with clinical stages of subjects in the CN, EMCI, LMCI, and AD groups (FIG. 7). All but one of the CN subjects had a CARE index value lower than 6, while all AD subjects had a CARE index value higher than 6. The CARE index values for EMCI and LMCI groups were between those of the CN and AD groups (FIG. 8A).

Specifically, the proportion of EMCI subjects that had a CARE index value between 0 and 5 was higher than that of the LMCI subjects, and the percentage of LMCI subjects that had a CARE index value between 6 and 10 was higher than that of the EMCI subjects. Statistically, CARE index value differences among groups were identified (FIG. 8B). The median CARE index value of the CN, EMCI, LMCI, and AD groups were 2, 4, 6, and 9, respectively. The CN group exhibited a lower CARE index value than the EMCI ($p<0.005$), LMCI ($p<0.5 \times 10^{-6}$), and AD ($p<0.1 \times 10^{-6}$) groups. The AD group showed a higher CARE index value than EMCI ($p<0.5 \times 10^{-4}$), and LMCI ($p<0.5 \times 10^{-4}$) groups. In addition, the EMCI group showed a lower CARE index value than the LMCI ($p<0.02$) group. Note that the association between CARE index values and clinical stages was applied to all of the data, including data for EMCI and LMCI subjects, who were not involved in the process for determining $S_{optimal}$.

Figure 9:
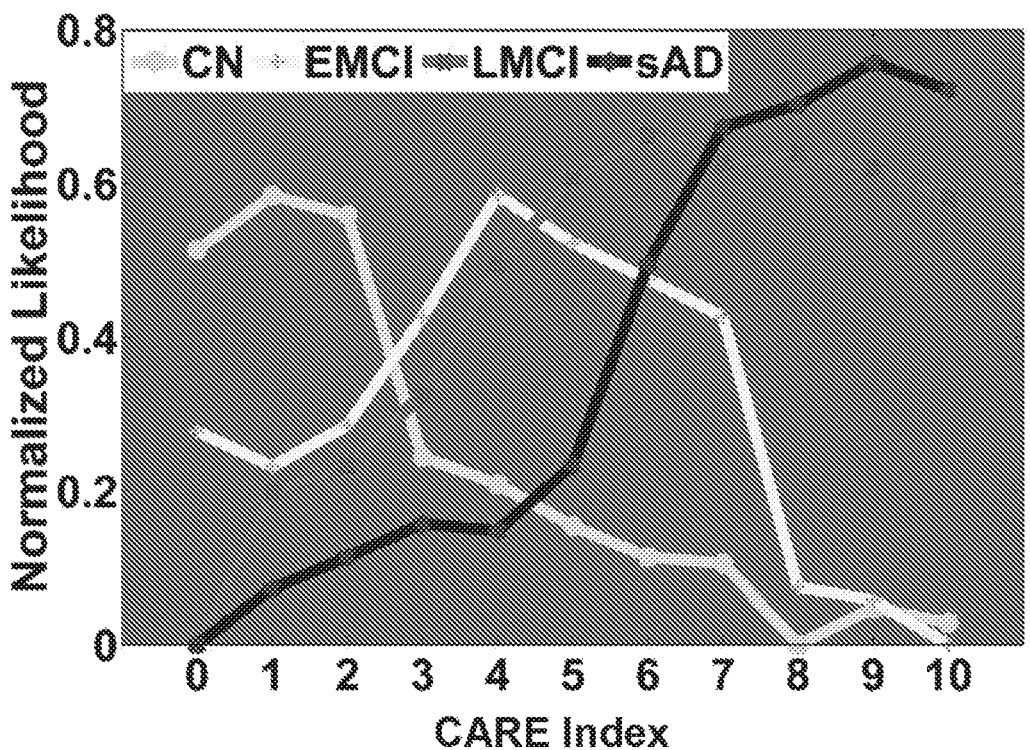
FIG. 9 depicts normalized likelihoods across CARE indices for an example study. The cyan, yellow, red, and black lines represent the likelihoods at each CARE index for a CN subject, an EMCI subject, a LMCI subject, and an AD subject, respectively.

Individual Normalized Likelihood Samples. Four typical subjects, one from each of the CN, EMCI, LMCI, and AD groups, were selected to illustrate the distribution of the normalized likelihoods at each CARE index (FIG. 9). The AD risk for each of the four subjects was determined by the position of the subject's highest likelihood value on the CARE index, where a value of 1 was associated with the CN subject, 4 with the EMCI subject, 7 with the LMCI subject, and 9 with the AD subject. Moreover, the curve provided likelihood values at other CARE index values, showing each subject's risk of developing AD. For example, the LMCI subject had relatively high likelihood (close to 0.6) at CARE index values 7, 8, and 9, in addition to the highest likelihood (0.65) at index value 6. This suggests that this LMCI subject has a high risk of progression from LMCI to AD-type dementia. Information of this nature may facilitate individual clinical inference.

Figure 10:
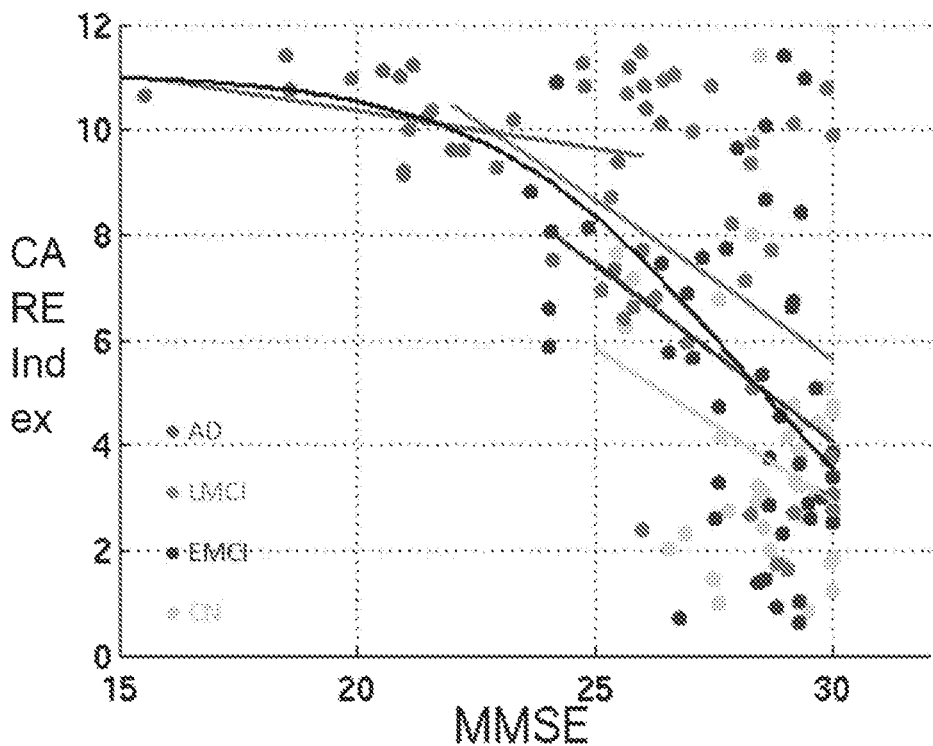
FIG. 10 depicts relationships between CARE index and cognitive severity. This relationship is statistically valid within the groups and across entire subjects, assessed either with linear regression model or nonlinear curve-fitting analysis. Note that, since the data are discrete, many individual data points overlap; for clarity, each of the individual plot points were perturbed by adding a small random displacement in the horizontal and vertical directions. The linear regression analysis used only the original (non-perturbed) data as an input.
Figure 11:
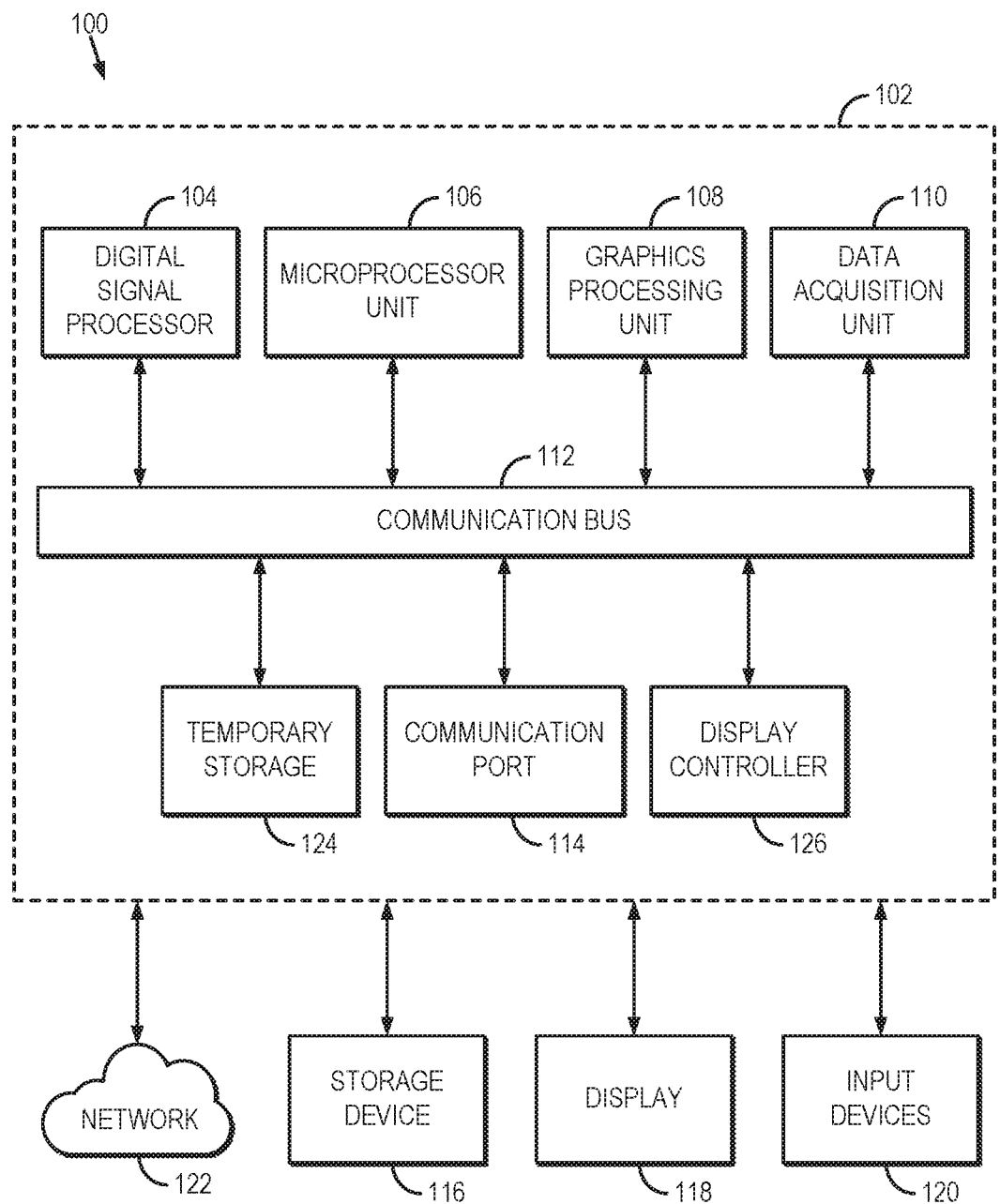
FIG. 11 is a block diagram of an example computer system that can implement the methods described herein.

MMSE Scores Correlated with CARE Index. The degree of the disease severity, represented by the MMSE score, was significantly correlated with the CARE index (FIG. 10). The full multiple linear regression model was significant ($p \leq 1.11e-18$). For the individual clinical group, regression lines were also significant for the CN ($p \leq 0.017$), EMCI ($p \leq 0.009$), and LMCI ($p \leq 0.041$) groups. For the AD group, such a relationship also showed a strong tendency ($p \leq 0.086$). The higher the CARE index value, the lower the MMSE score and the more sever the disease. This relationship was statistically valid between and within the subject groups. The curve fitting was estimated using a nonlinear least squares algorithm, yielding b0=3.47, A=10.32, and k=0.12. The F-statistic for the full exponential model fit was F[2,141]=48.85, with corresponding p-value=1.11e−16. The CARE index vs. MMSE data scatter plot is shown in FIG. 10 (black line).

Figure 13A:
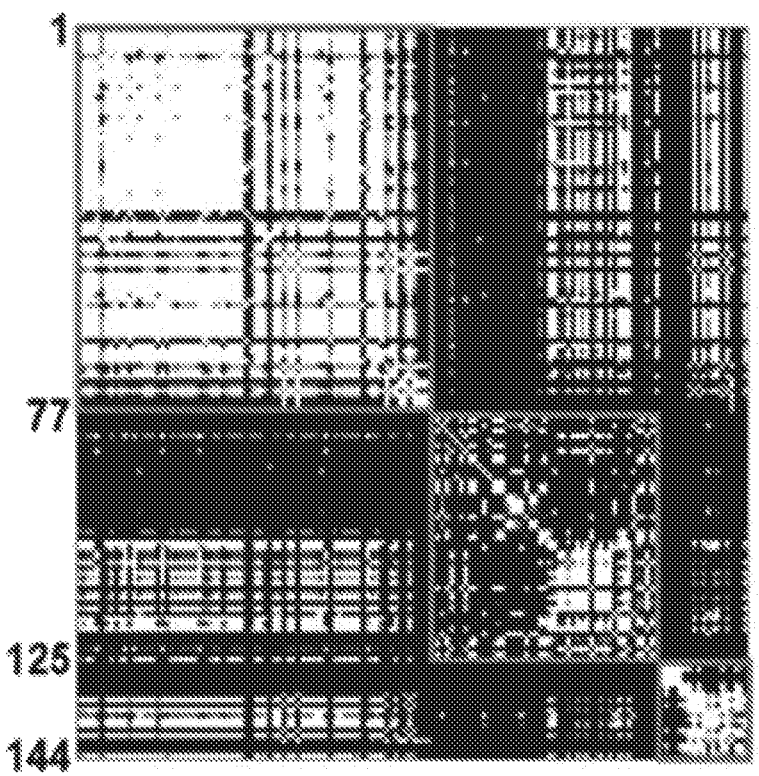
FIG. 13A is an example output of a hierarchical clustering algorithm that illustrates three classified groups of subjects associated with three distinct AD progressions.

Preliminary results of classifying the subtypes of AD disease pathways. Following the methods described above, in one example the ADNI 2 datasets and the results described above were used to classify the individuals into three subtypes. By comparing the cross correlation coefficient between each pair of individuals' $S_j^{optimal}$ using hierarchical clustering methods, FIG. 13A illustrates that in this example there were three clusters. With BFM, each cluster has its own optimal sequences of biomarker events.

Figure 13B:
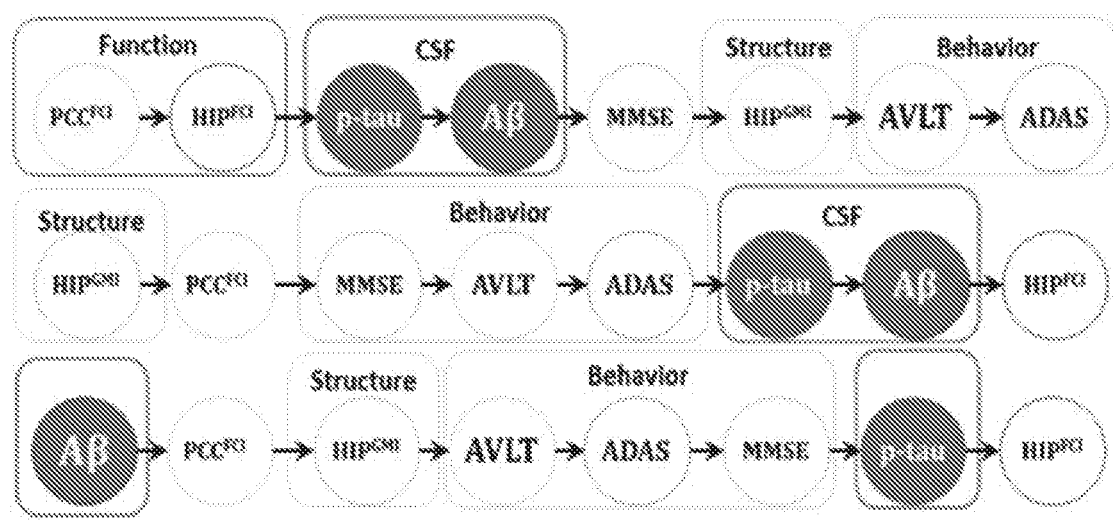
FIG. 13B is an example diagram representing the temporal ordering sequences associated with the clusters illustrated in FIG. 13A.

The estimated $S_{c1}^{optimal}$ for the first subtype is shown in the top row of FIG. 13B. Two functional biomarkers: $HIP^{FCI}$ and $PCC^{FCI}$ were the lead events to be abnormal in this subtype, followed by two CSF molecular biomarkers: $A\beta_{1-}$ 42 and p-tau. The next events were a mix of memory related cognitive and structure biomarkers: MMSE, and $HIP^{GMI}$. The last events were two behavior biomarkers: AVLT and ADAS.

The estimated $S_{c2}^{optimal}$ for the second subtype is shown in the middle row of FIG. 13B. The leading events were neurodegenerative structural and functional related biomarkers of $HIP^{GMI}$ and $PCC^{FCI}$, followed by behavioral biomarkers of MMSE, AVLT and ADAS, then by CSF pathological biomarkers: $A\beta_{1-42}$ and p-tau, the last was memory related functional biomarker, $HIP^{FCI}$.

The estimated $S_{c3}^{optimal}$ for the third subtype is shown in the bottom row of FIG. 13B. In this third subtype, $A\beta_{1-42}$ showed as abnormal first, followed by $PCC^{FCI}$, $HIP^{GMI}$, and memory and cognitive related biomarkers of AVLT, ADAS and MMSE. The p-tau became abnormal at very late phase of the sequence with memory related functional biomarker of $HIP^{FCI}$. The first subtype contained the majority (e.g., 53%) of the population in the ADNI 2 datasets, whereas the second subtype was 34% of the population and the third subtype was 13% of the population. According to the different locations of the $A\beta_{1-42}$ and p-tau in sequences relative to the locations of other biomarkers, the first subtype sequence was assigned for the typical AD progression, the second subtype sequence was assigned for the SNAP progression, and the third subtype sequence was assigned for the normal aging processes.

These results are supported by most recent suggestions that although amyloidosis and neurodegeneration arise independently, once both are present, they interact to accelerate the AD pathophysiological cascade and are a key mechanism in transforming normal aging into AD. The reason the second subtype was assigned as the SNAP progression is that not only the abnormal degenerative biomarkers occurred before the pathological biomarkers, but also the role of β-amyloid is to induce the propagation of tauopathy, rather than to initiate the first tau deposition, as previously described. As shown in the third subtype, because $A\beta_{1-42}$ and p-tau are far apart in the sequence, the risk to develop AD would be substantially reduced.

The $S_{optimal}$ of dynamic biomarkers, estimated herein exhibits great potential in clinical applications. At the symptom-based group level, the average CARE index value of each clinical group was significantly different than that of the other groups. The results of this study demonstrate that the biomarker-based CARE index is in parallel with disease severity indicated generally by symptom-based clinical stages. In comparison, traditional clinical-symptoms-based staging methods at group level are limited in that the subjects in each group comprise a biologically heterogeneous population, which poses a great challenge for disease prevention, diagnosis, and treatment.

The present study offered a novel approach in that it uses the CARE index to characterize the risk of AD events at the individual level and does not rely on information from a clinical diagnosis or a specific level of biomarker "cutpoint." It is contemplated that this capability will facilitate clinical trials by identifying individual subjects that have no clinical symptoms but remain at risk for developing AD; selecting the right segmentation of patient populations, based on their CARE index values, to enrich response rates, as has been demonstrated in other medical fields such as in oncology; and monitoring and evaluating treatment efficacy through changes in CARE index value in individual subjects. This personalized medicine technique would be particularly beneficial in assessing the efficacy of promising secondary prevention interventions in patients at the earliest discernible stage of AD.

In this study, it was demonstrated that the average CARE index values of the EMCI and LMCI groups of subjects are in line with symptom-based staging, and the individual CARE index values were significantly correlated with disease severity, as measured by MMSE scores, in the full disease spectrum (i.e., CN, EMCI, LMCI, or AD). Whereas, no single biomarker has been found that can measure disease severity across the full disease spectrum (for example, the $A\beta_{1-42}$ biomarker does not significantly correlate with cognitive scores), the CARE index has the capability to predict disease severity. The higher the CARE index value, the more advanced and severe the disease. Compared with symptom-based disease stages, the CARE index provides higher temporal resolution to define the disease developmental processes. With the strength of significant correlation between stage and disease severity, the CARE index could be a surrogate index used to assess treatment efficacy on the individual level.

The example study described above was a first attempt to incorporate the resting state functional connectivity $HIP^{FCI}$ and $PCC^{FCI}$ biomarkers into an EBP model to estimate $S_{optimal}$ and determine the EBP model-based AD stages on individual basis. In fact, a number of other functional and structural biomarkers, such as the executive control network, salience networks, and insular networks, can also be integrated into the biomarker ordering sequence. It is contemplated that the inclusion of these networks could advantageously characterize the trajectory of where, when, and how the neural network changes with AD progression. In addition, the methods to measure these biomarkers can be extended from the current ROI-based analysis to the independent component analysis, graph theory, or network modular analysis.

Example 2

In this example study, the effects of missing biomarker information for an individual subject on measuring Alzheimer's disease risk staging was performed.

Example 2: Methods

Subject Information. This study employed data from the Alzheimer's Disease Neuroimaging Initiative-2 (ADNI-2) database. For the study, 70 subjects were selected from the ADNI-2 database based on the following requirements. First, all subjects had at least one resting-state functional connectivity magnetic resonance imaging (R-fMRI) scan with corresponding anatomical scans. Second, all subjects had cerebrospinal fluid (CSF) Aβ and phosphorylated tau (p-tau) concentration values. Third, all subjects had scores on the Mini-Mental State Examination (MMSE), modified 13-item Alzheimer's Disease Assessment Scale-Cognitive Subscale (ADAS-Cog), and Rey Auditory Verbal Learning Test (AVLT) (immediate recall score, i.e., the sum of trials 1 to 5). Together, the 70 subjects included 45 CN, and 25 Alzheimer's disease subjects.

A total of 10 biomarkers were selected and justified as discussed below. The justification to select these biomarkers, or "events," is that no single biomarker can link the pre-clinical stage to the clinical stage of AD. The two CSF molecular biomarkers (Aβ and p-tau) indicate the preclinical events that have been extensively studied in AD research over the last two decades to test the Aβ cascade hypothesis.

Three cognitive biomarkers were selected as the downstream events (MMSE, Rey AVLT summation (RAVLTsum), and the ADAS-Cog) to measure clinical manifestation of AD progression. Two structural biomarkers, brain gray matter concentration indices (GMI) in the bilateral hippocampi ($HIP^{GMI}$) and the bilateral fusiform gyri ($FUS^{GMI}$), were also incorporated to detect the "downstream" effect of structural changes during the disease progression. Three functional connectivity indices (FCI) were also integrated as biomarkers measured by R-fMRI in the bilateral posterior cingulate cortex (PCC) ($PCC^{FCI}$) in the default mode networks (DMN), the bilateral hippocampus functional networks ($HIP^{FCI}$), and the bilateral fusiform gyrus functional networks ($FUS^{FCI}$). The hyperconnectivity index of fusiform networks was also used as one of the three functional biomarkers for staging the risk of AD in this study.

Because the specific spreading patterns of AD pathologies are through neural network connections, it was a hypothesis of this study that the sequential and progressive disease events during the pathological spreading can be characterized by the changes in the network patterns detected by R-fMRI biomarkers. These changes may be upstream or downstream to link preclinical stages to the emergence of overt symptomatology and predict the subsequent clinical decline.

Imaging Acquisition. The ADNI data acquisition process is described at http://adni.loni.ucla.edu/. Briefly, R-fMRI datasets were scanned on 3.0 Tesla (T) MRI scanners (Philips, Netherlands). During the resting-state acquisitions, no specific cognitive tasks were performed, and the participants were instructed to relax with their eyes open inside the scanner. Axial R-fMRI images of the whole brain were obtained in seven minutes with a single-shot gradient echo planar imaging (EPI) sequence. High-resolution MP-RAGE (magnetization-prepared rapid gradient-echo) 3-D sagittal images also were acquired.

Resting-State Image Preprocessing. Conventional preprocessing steps were conducted using Analysis of Functional NeuroImages (AFNI) software (http://afni.nimh.nih.gov/afni/), SPM8 (Wellcome Trust, London, United Kingdom), and MATLAB (MathWorks, Natick, Mass.). The preprocessing allows for T1-equilibration (removing the first 15 seconds of R-fMRI data); slice-acquisition-dependent time shift correction (3dTshift); motion correction (3dvolreg); detrending (3dDetrend); despiking (3dDespike); spatial normalization (original space to the Montreal Neurological Institute [MNI] space, SPM8); averaging white matter and cerebrospinal-fluid (CSF) signal retrieval (3dROIstats) using standard SPM white matter and CSF mask in the MNI space; white matter, CSF signal, and motion effect removal (3dDeconvolve); global signal removal necessity check (the global signal will be removed if necessary) [16]; and low-frequency band-pass filtering (3dFourier, 0.015-0.1 Hz).

Biomarker Events. Ten well-studied Alzheimer's disease biomarkers, as described above were selected (Table 2), each representing an event that occurs along with Alzheimer's disease progression.

Weighted average stage. The mathematical detail of the Event-Based Probabilistic (EBP) model is described above. The EBP model determines the optimal order of biomarker events (i.e., $S^{optimal}=\{E1, E2, E3, E4, E5, E6, E7, E8, E9, E10\}$). It also determines the likelihood of subject j being in stage k given the biomarker measurement $X_j$ and $S^{optimal}$, by the formula in Eqn. (5).

Multiple linear regression was employed to study the relationship between weighted average stage and the stage calculated with the original method. The $R^2$ value was calculated to study the relationship, where R is the Pearson product-moment correlation coefficient.

$S^{optimal}$ in missing biomarkers. In the EBP model described above with respect to FIG. 2, the individual subject's disease stage was determined by a "winner take all" approach, in which the stage k with the highest likelihood value determines the subject's disease stage. However, when there is one or more missing biomarkers, this will pose a potential problem. For example, when a subject's disease stage corresponds to the missing marker k, it will be impossible to determine the subject's disease stage to be k in the "winner take all" approach. The disease stage will fall to the next available highest likelihood stage, most likely k−1 or k+1. To address this problem, the weighted average stage defined above is used. Theoretically, the weighted average stage of a subject can still be k even when the corresponding marker is missing, this is demonstrated with a representative subject below.

In the case of missing biomarker missing $i_{missing}$, $p(x_{i_{missing}}|E_{s(i_{missing})})$ and $p(x_{i_{missing}}|\neg E_{s(i_{missing})})$ were set to be 1. This is equivalent of taking them out of Eqn. (5) without having to modify the existing programs. Meanwhile, for $k=i_{missing}$, $p(X_j|S, k)$ was set to be 0. With these numerical modifications, neither the analytical equations described above, nor the existing programs needed to be modified. However for clarity, Eqn. (5) can be rewritten for the case of missing biomarker(s).

$$p(X_j|S,k)=0, k=i_{missing}$$

$$p(X_j|S,k)=\Pi_{i=1}^{k}p(x_{ij}|E_{s(i)})\Pi_{i=k+1}^{N}p(x_{ij}|\neg E_{s(i)}), i\neq i_{missing}$$

The program was employed to calculate $S^{optimal}$ when the biomarkers were missing. The weighted average stage for each subject was calculated for four different optimal order of remained biomarker event, $S^{optimal}$, $S_{missing\ A\beta}^{optimal}$, $S_{missing\ ptau}^{optimal}$ and $S_{missing\ A\beta, ptau}^{optimal}$.

Effect of missing biomarkers on CARE index score. Multiple linear regression was employed to study the effect of missing biomarkers on CARE index score. The $R^2$ value was calculated from the weighted average stages of different optimal order of biomarker events, i.e. $S^{optimal}$ and $S_{missing\ A\beta}^{optimal}$, $S_{missing\ ptau}^{optimal}$, $S^{optimal}$ and $S_{missing\ A\beta, ptau}^{optimal}$.

Example 2: Results

Optimal sequence of events with missing data. The optimal sequence of events S was calculated when the biomarkers were missing. In the case of missing $A\beta_{1-42}$ biomarker, S becomes $$S_{missing\ A\beta}^{optimal}=\{E1, E2, E4, E5, E6, E7, E8, E9, E10\}$$

TABLE 2

The order often progressive events in Alzheimer's disease development represented by the ten well-studied biomarkers.

| E1 | E2 | E3 | E4 | E5 | E6 | E7 | E8 | E9 | E10 |
| --- | --- | --- | --- | --- | --- | --- | --- | --- | --- |
| $HIP^{FCI}$ | $PCC^{FCI}$ | $A\beta_{1-42}$ | p-tau | MMSE | ADAS-Cog | AVLT | $HIP^{GMI}$ | $FUS^{GMI}$ | $FUS^{FCI}$ |

In the case of missing p-tau biomarker, S becomes $$S_{missing\ ptau}^{optimal} = \{E1,E2,E3,E5,E6,E7,E8,E9,E10\}$$

In the case of missing both $A\beta_{1-42}$ and p-tau biomarker, S becomes $$S_{missing\ A\beta,ptau}^{optimal} = \{E1,E2,E5,E6,E7,E8,E9,E10\}$$

The relative order of residual biomarkers was not affected by the removal of missing biomarkers from the model.

Figure 14:
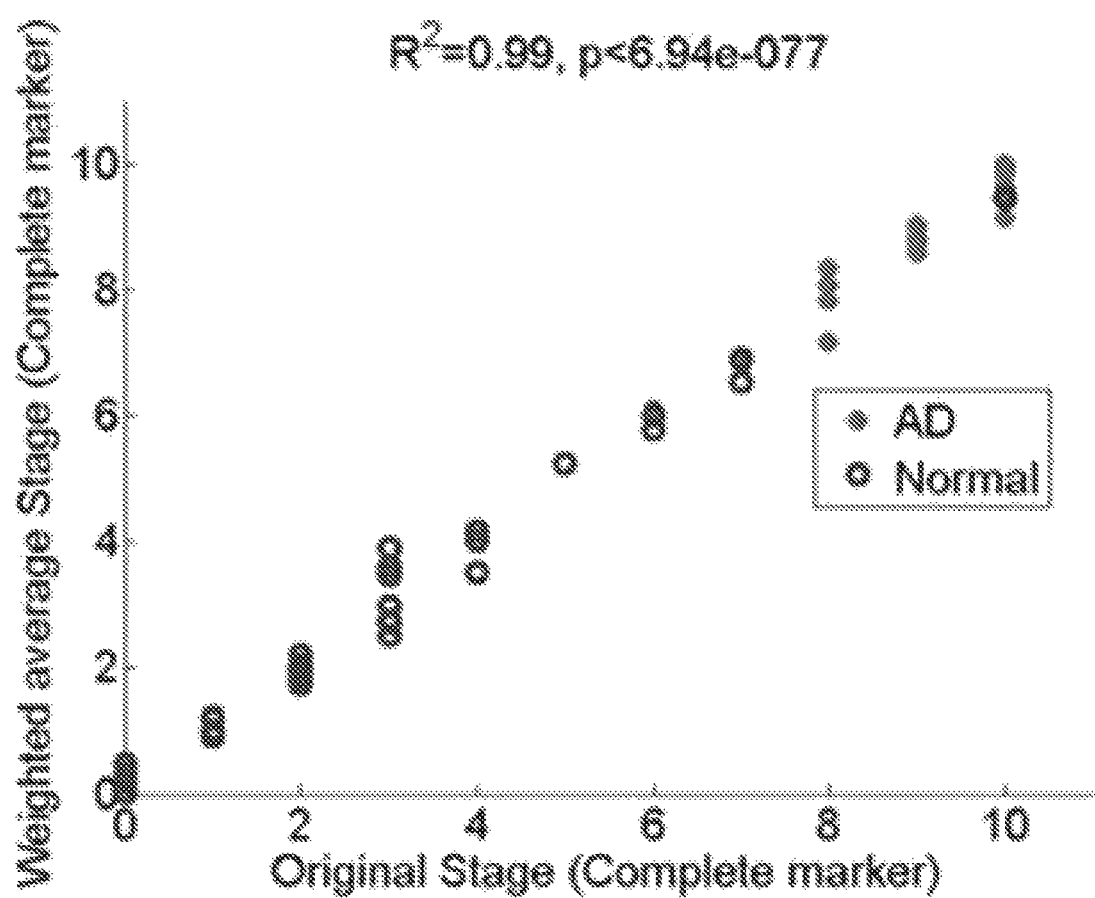
FIG. 14 shows a relationship between the stages calculated with a weighted average method and a non-weighted average method for a complete set of biomarkers.

Weighted Average (WA) Stage Method. Multiple linear regression analysis was employed to study the relationship between WA stage and the original stage. FIG. 14 shows the strong linear relationship between the stages calculated with the original and weighted average methods when the biomarkers are complete.

Figure 15C:
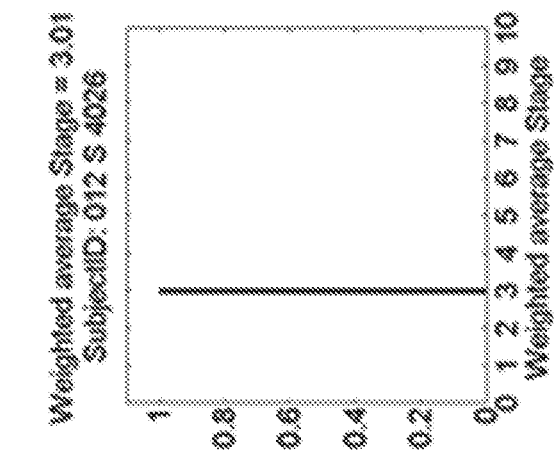
FIG. 15C shows the subject's weighted average stage selected as 3.01 using a weighted average of the stages shown in FIG. 15B, Stage=0×0+1×0.37+2×0.34+3×0+4×0+5×0.03+6×0.01+7×0.25+8×0+9×0+10×0=3.01.
Figure 15B:
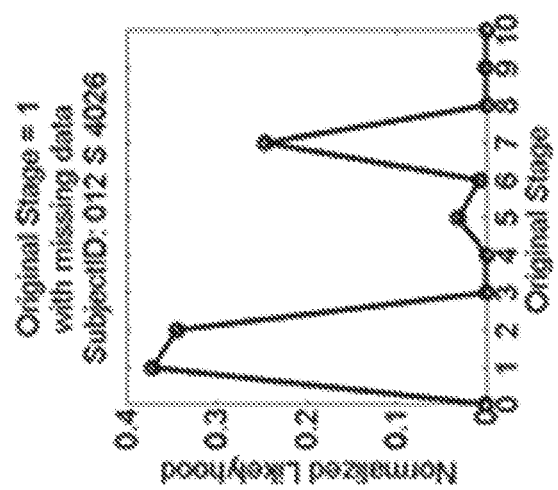
FIG. 15B shows the subject's stage selected as "1" using incomplete data.
Figure 15A:
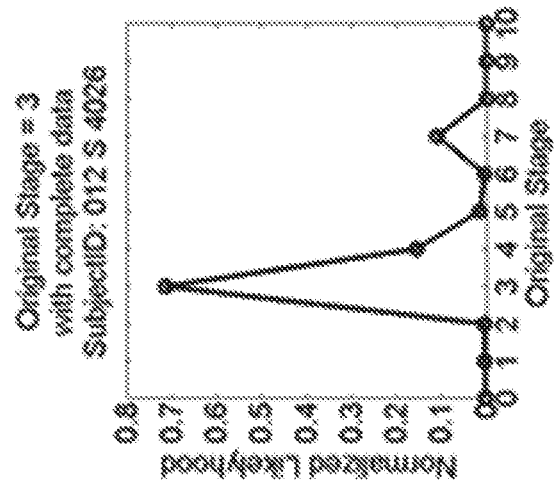
FIG. 15A shows a subject's stage selected as "3" using complete biomarker data.

By employing the weighted average method, practically, the stage for an individual subject can still be k even when the corresponding k biomarker is missing. As shown in FIGS. 15A-15C, the subject's original stage is 3 with complete data (FIG. 15A), the subject's stage becomes 1 with missing data at stage 3 and 4 if still using the non-weighted average method (FIG. 15B). With missing data of $A\beta$ and p-tau, the normalized likelihoods of remained stages of 1, 2, 5 and 7 are bigger and maxed at stage 1. In contrast, with the weighted average method, the subject's weighted average stage shown in FIG. 15C is 3.01, calculated as the weighted average of the stages shown in FIG. 15B. The difference has only 0.01 under missing data condition, compared with the original stage of 3.

Figure 16:
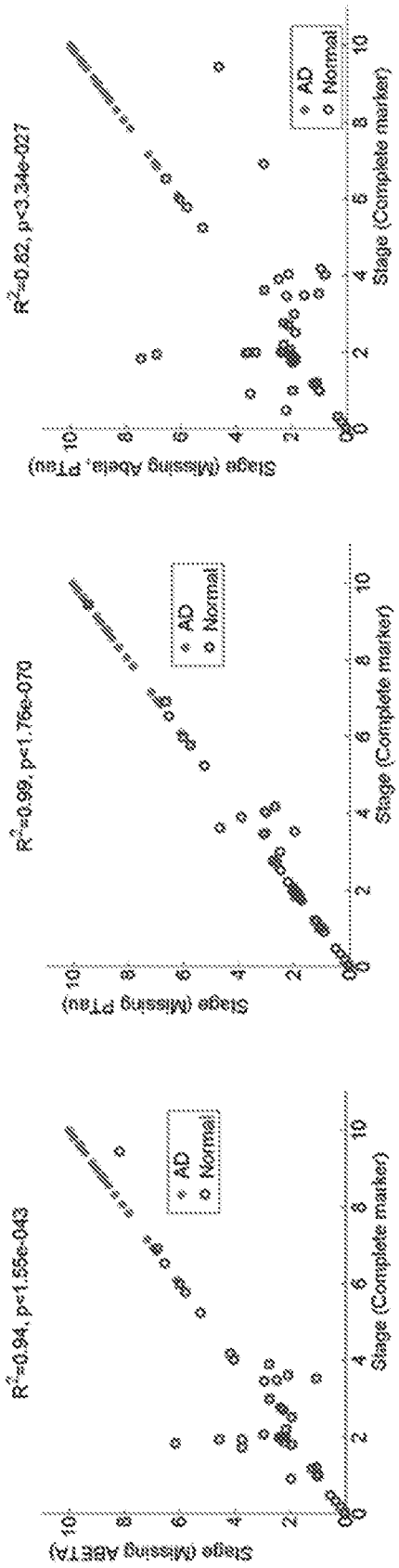
FIG. 16 shows the effect of missing biomarkers, specifically, the linear relationship between the weighted average stages calculated from different optimal order of biomarker events.

Effect of missing biomarkers on AD stages. Multiple linear regression was employed to study the effect of missing biomarkers on AD stages. FIG. 16 shows the linear relationship between the weighted average stages calculated from different optimal order of biomarker events. The linear relationship is strong. But the fact of missing biomarkers do introduce noticeable variations (measured by 1-R^2). For example, missing $A\beta$ will introduce 6% of variation; missing p-tau will introduce 1% of variation; and missing both biomarker will introduce 18% of variation; In this case, the effect of missing two biomarkers together is bigger than sum of the effects of missing one biomarker individually. Although the majority of subjects remained in their original stages, several other subjects showed a discrepancy. Those subjects with original stages 3 and 4, have decreased to stage 3 and 2 respectively, two subjects with original stage 2 have increased to stage 7, and two subjects with original stage 7 and 10 have decreased to stage 3 and 5.

Figure 17:
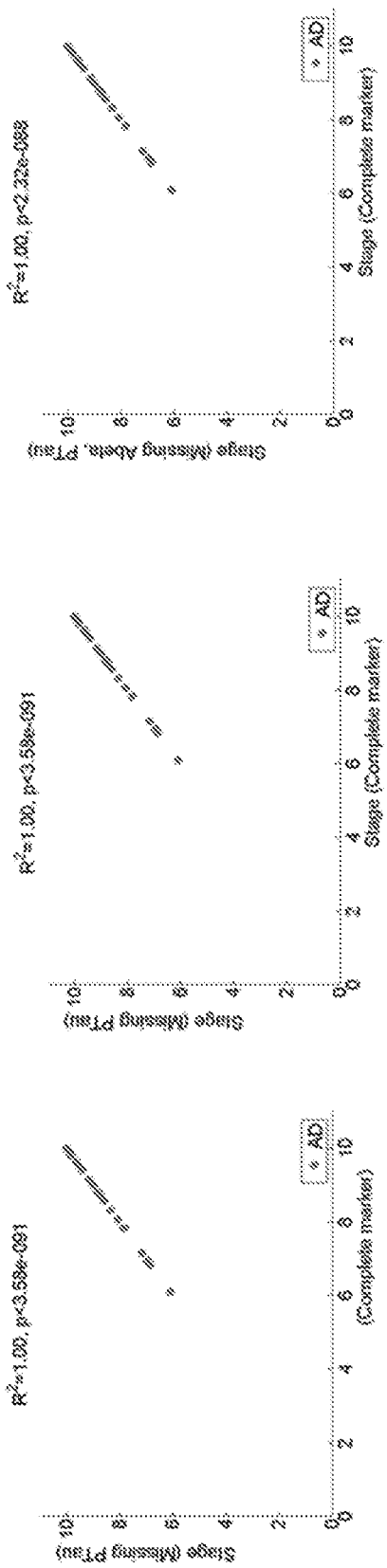
FIG. 17 shows the effect of missing early biomarkers on late stage measurement.

Effect of missing early stage biomarkers on late stage measurement. Multiple linear regression was employed to study the effect of missing early stage biomarkers on late stage measurement. FIG. 17 shows the linear relationship between the weighted average stages calculated from different optimal order of biomarker events for only the Alzheimer's disease subjects. The linear relationship is very strong. The fact of missing early biomarkers did not introduce any noticeable variations for the late stage subjects (i.e., Alzheimer's disease).

Example 3

Figure 18:
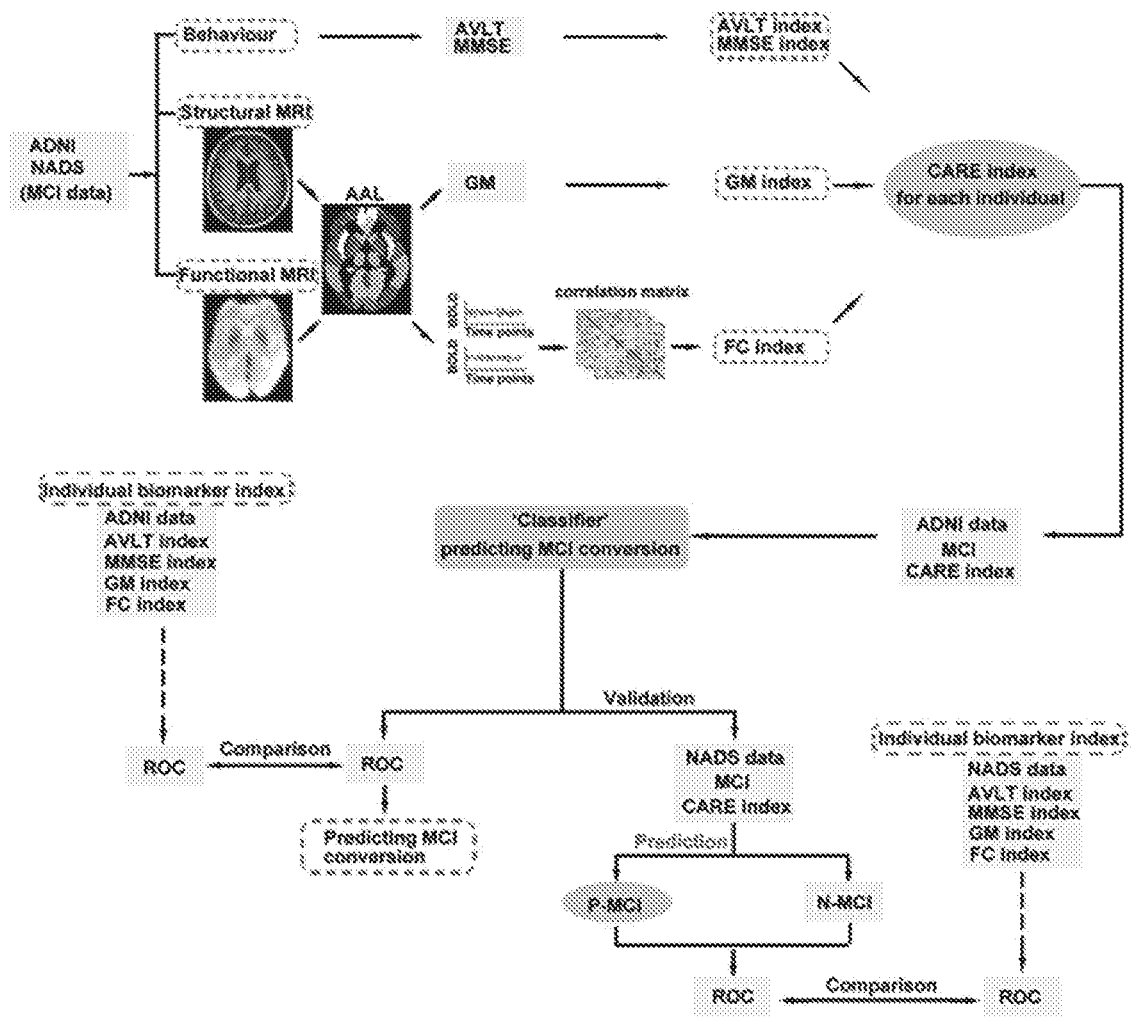
FIG. 18 shows a flowchart setting forth the steps of a classification, rigorous cross-validation, and prediction framework across datasets. First, each individual CARE index score is calculated for MCI subjects in the ADNI and NADS datasets. Second, CARE index stage is adopted for classification of N-MCI and P-MCI in the ADNI dataset. Third, the "classifier" of CARE index stage determined from the ADNI dataset is applied to predict the conversion of MCI subjects in the NADS dataset. An ROC curve is used to assess the performance of classifier classification of CARE index stage and classifier prediction of CARE index stage, respectively. In addition, the differences of performance of classification and prediction of CARE index stage and original indices (AVLT, MMSE, GM, and FC indices) can be compared by comparing the ROCs of them across datasets.

In this example study, the CARE index was used to distinguish those mild cognitive impairment ("MCI") individuals who progressed to AD-type dementia from those who did not from the ADNI during a 3-year follow-up period and subsequently generalized the CARE index on for the prediction of MCI individuals from the independent Nanjing Aging and Dementia Study ("NADS") dataset during the same time-period. In this study, it was hypothesized that the CARE index score accurately predicted MCI-to-AD progression with high sensitivity and specificity at the individual patient level over three years in the ADNI dataset. It was also hypothesized that the excellent prediction performance of the CARE index could be validated in the independent NADS dataset during the same time-period. To test these hypotheses, using widely available, cost-effective, non-invasive biomarkers from behavioral, brain structural and functional levels, we defined each subject's CARE index score as the order number showing the highest likelihood value in the biomarkers sequence. FIG. 18 shows a flowchart that summarizes the experimental procedures that were conducted in this study.

Example 3: Methods

Subjects. Study subjects were selected from two independent datasets: the Alzheimer's Disease Neuroimaging Initiative (ADNI) and Nanjing Aging and Dementia Study (NADS).

ADNI. From the ADNI-2 database, a total 74 MCI subjects with a baseline diagnosis of amnestic MCI were selected based on the following requirements. First, all subjects had at least one resting-state functional magnetic resonance imaging (R-fMRI) scan with corresponding anatomical scans. Second, all subjects had cerebrospinal fluid (CSF) $A\beta$ and phosphorylated tau (p-tau) concentration values. Third, all subjects had scores on the Mini-Mental State Examination (MMSE), modified 13-item Alzheimer's Disease Assessment Scale-Cognitive Subscale (ADAS-Cog), and Rey Auditory Verbal Learning Test (AVLT) (immediate recall score, i.e., the sum of trials 1 to 5). Of note, in this study, the CSF, p-tau, and ADAS-Cog biomarkers were only used to estimate the optimal temporal sequence of events by using event-based probabilistic model. Finally, in this study, 46 subjects had a 3-year follow-up clinical diagnosis of MCI and met criteria for inclusion as part of either non-progressive MCI (N-MCI) group, including MCI subjects who did not progress to AD-type dementia at 3-year follow-up or progressive MCI (P-MCI) group, including MCI subjects who progressed to AD-type dementia at 3-year follow-up. At study entry (baseline), all subjects underwent a standardized clinical interview, cognitive/functional assessments, structural MRI, and R-fMRI scans. Subjects were then followed longitudinally at specific intervals (36 months). The clinical status of each MCI subject was re-evaluated at 36-month follow-up time point and updated to reflect one of several outcomes (normal control, MCI, and AD). According to the follow-up clinical diagnosis by the NINCDS-ADRDA criteria for the diagnosis of probable AD, those MCI subjects who progressed to AD-type dementia within 36 months of entering the study were labeled as P-MCI, those not progressed as N-MCI subjects. The clinical status for N-MCI and P-MCI subjects is employed as the "ground truth" in the classification experiments as described below. Note that most of included subjects in the ADNI dataset had not met both scores of comprehensive neuropsychological assessment and at least one R-fMRI scan with corresponding anatomical scans at 3-year follow-up. Therefore, data from ADNI dataset were not used to investigate the links between the changes of characterizing AD risk event and the changes of neuropsychological performance.

NADS. The NADS study recruited 87 subjects with a baseline diagnosis of amnestic MCI status, through normal community health screening, newspaper advertisement, and hospital outpatient service.

All MCI subjects were evaluated by memory-disorders physicians. Of the 87 subjects, 56 had a 3-year follow up clinical diagnosis of MCI and met criteria for inclusion as part of either the P-MCI or N-MCI group in this study.

Subjects were followed longitudinally for 36 months. The clinical status of each MCI subject was re-evaluated at 36-month follow-up time point and updated to reflect one of several outcomes (normal control, MCI, and AD). The clinical diagnosis of MCI and AD status was based on a standardized clinical interview, including demographic inventory, medical history, neurological and mental status examination, laboratory findings, and imaging studies routinely performed as part of the clinical assessment of dementia. This follow-up clinical diagnosis was made by the same memory-disorders physicians, who were blind to our study data. These MCI subjects were separated into the N-MCI and P-MCI groups as described above.

Neuropsychological assessment. In the NADS dataset, all subjects underwent a standardized clinical interview and comprehensive neuropsychological assessments at baseline and 3 years follow-up that were performed by neuropsychologists. These tests were used to evaluate multi-domains of cognitive function, including general cognitive function, episodic memory, information processing speed, executive function, and visuo-spatial function.

MRI data acquisition. The ADNI data acquisition process is described at http://adni.loni.ucla.edu/. Briefly, R-fMRI datasets were scanned on 3.0 Tesla MRI scanners (Philips, Netherlands). During the resting-state acquisitions, no specific cognitive tasks were performed, and the participants were instructed to relax with their eyes open inside the scanner. Axial R-fMRI images of the whole brain were obtained in seven minutes with a single-shot gradient echo planar imaging (EPI) sequence. High-resolution MP-RAGE (magnetization-prepared rapid gradient-echo) 3-D sagittal T1-weighted images also were acquired. For the NADS dataset, MRI images were acquired using a 3.0 Tesla Verio Siemens scanner (Siemens, Erlangen, Germany) with a 12-channel head-coil at ZhongDa Hospital Affiliated to Southeast University.

Resting-state image preprocessing. Conventional preprocessing steps were conducted using Analysis of Functional NeuroImages (AFNI) software (http://afni.nimh.nih.gov/afni/), SPM8 (Wellcome Trust, London, United Kingdom), and MATLAB (MathWorks, Natick, Mass.). The preprocessing allows for T1-equilibration (removing the first 15 seconds of R-fMRI data); slice-acquisition-dependent time shift correction (3dTshift); motion correction (3dvolreg); detrending (3dDetrend); despiking (3dDespike); spatial normalization (original space to the Montreal Neurological Institute [MNI] space, SPM8); averaging white matter and CSF signal retrieval (3dROIstats) using standard SPM white matter and CSF mask in the MNI space; white matter, CSF signal, and motion effect removal (3dDeconvolve); global signal removal necessity check (the global signal will be removed if necessary) (Chen G et al. 2012); and low-frequency band-pass filtering (3dFourier, 0.015-0.1 Hz).

Biomarker events, expected stage, and missing biomarker. As described above, ten well-studied AD biomarkers were selected, each representing an event that dynamically occurs along with AD progression from preclinical phase to the overt of dementia. These biomarkers include three region-based R-fMRI functional connectivity indices (FCI) from the hippocampus (HIPFCI), the posterior cingulate cortex (PCCFCI), and the fusiform gyrus (FUSFCI); two gray matter concentration indices (GMI) from the hippocampus (HIPGMI) and fusiform gyrus (FUSGMI); two CSF biomarkers of Aβ1-42 and p-tau levels; and three cognitive biomarkers of MMSE, ADAS-Cog, and AVLT scores.

The optimal temporal sequence, $S^{optimal}$, is determined by the event-based probabilistic (EBP) model described above. In the case of missing biomarkers, an alternative method useful for determining the $S^{optimal}$ of biomarker events with missing data is described above. Note that in this study, three biomarkers (two CSF biomarkers of Aβ1-42 and p-tau levels and ADAS-Cog scores) were missing in the NADS dataset. For consistency between the ADNI and NADS datasets to compute the CARE index, these three biomarkers in the ADNI dataset were not employed. Therefore, in this study, the remaining seven biomarkers were integrated into the CARE index using the weighted average method described above because they were widely available, cost-effective, and non-invasive biomarkers.

Individual CARE index. Each of the 10 biomarker events were numbered by the order of occurrence in the $S^{optimal}$; collectively, these events form the CARE index. Each subject's CARE index score is defined as that at which the order number had the highest likelihood value in the $S^{optimal}$. Each subject's CARE index score represents the subject's AD risk stage.

Statistical Analysis-Demographic and Neuropsychological Data.

The statistical analyses were conducted with SPSS 22.0 software. The two-sample t-test, chi-square ($\chi2$) test, Mann-Whitney U tests were used to compare the differences in demographic data, neuropsychological performances, each individual biomarker feature and the CARE index between N-MCI and P-MCI.

Statistical Analysis-MCI conversion prediction. The power of the CARE index and of individual biomarkers to discriminate P-MCI from N-MCI were evaluated with the use of Receiver Operating Characteristic (ROC) curves. To demonstrate the CARE index's power for predicting the clinical progression of MCI to AD, the area under the ROC values (AUC) were employed to compare between CARE index and individual biomarkers using a non-parametric method for correlated samples. The optimal cutoff value of the CARE index for classifying P-MCI from N-MCI was extracted from the ADNI dataset, generating optimal sensitivity and specificity values, accuracy, odds ratio (OR), and relative risk (RR). Furthermore, the CARE index classifier obtained from ADNI dataset above was applied to the NADS dataset for validating the generalizability of the classifier in discriminating between P-MCI and N-MCI subjects.

To compare the stability and generalizability of the CARE index to classify between P-MCI and N-MCI subjects with those of individual biomarkers, the optimal classifier of each biomarker obtained from the ADNI dataset was also applied to the NADS dataset. To avoid unbalanced class frequency to lead to discrepancies between sensitivity and specificity, the balanced accuracy was also reported, where the balanced accuracy is defined as (sensitivity+specificity)/2. To directly observe the power of each biomarker in distinguishing P-MCI from N-MCI across datasets, the AUC, optimal sensitivity and specificity, accuracy, and balanced accuracy of the CARE index and individual biomarkers were ranked.

In addition, to avoid the limitations due to the relatively small sample size and the differences in the predictive power of the CARE index between the ADNI and NADS cohorts due to the differences of MCI heterogeneity in general, a supplementary analysis with combined cohort of ADNI and NADS datasets to evaluate the power of the CARE index to discriminate P-MCI from N-MCI was also performed.

Behavioral significance of the changes in CARE index measured at baseline and 3-year follow-up. To assess the behavioral significance of the changes in CARE index measured at baseline and 3-year follow-up, a multiple linear regression model analysis was performed to examine the relationships between the changes in CARE index and the changes in cognitive performance or clinical variables in MCI patients. To increase statistical power by reducing random variability, the neuropsychological tests were composited into four cognitive domains and the raw scores were transformed into four composite Z-scores.

Example 3: Results

Baseline demographic, neuropsychological characteristics, and CARE index. As expected, in the ADNI dataset, N-MCI and P-MCI showed no significant differences in age, gender, education, and MMSE scores (p>0.05). Compared with N-MCI, P-MCI showed significant deficits in performance in episodic memory (AVLT) and Alzheimer's Disease Assessment Scale-Cognitive Subscale (ADAS-Cog) tests (p<0.05). In the NADS dataset, P-MCI showed no significant differences in gender and education (p>0.05), but higher age and lower MMSE scores than N-MCI (p<0.05). Compared with N-MCI, P-MCI showed significant deficits in performance in multiple domains of cognitive functions, including episodic memory, information processing speed, and executive function (all p<0.05). Furthermore, both ANDI and NADS datasets showed that CARE index proved to differentiate well P-MCI from N-MCI at baseline (see FIGS. 19A-19C).

In the ADNI dataset, of the 46 MCI patients who entered into the study, 12 (26.1%) converted to AD and 34 (73.9%) did not convert during the 3-year follow-up period. In the NADS dataset, of the 56 MCI patients, 16 (28.6%) converted to AD and 34 (71.4%) did not convert during the 3-year follow-up period. Furthermore, there was no difference in the conversion rates of different MCI state transitions between the ADNI and NADS datasets.

Figure 19:
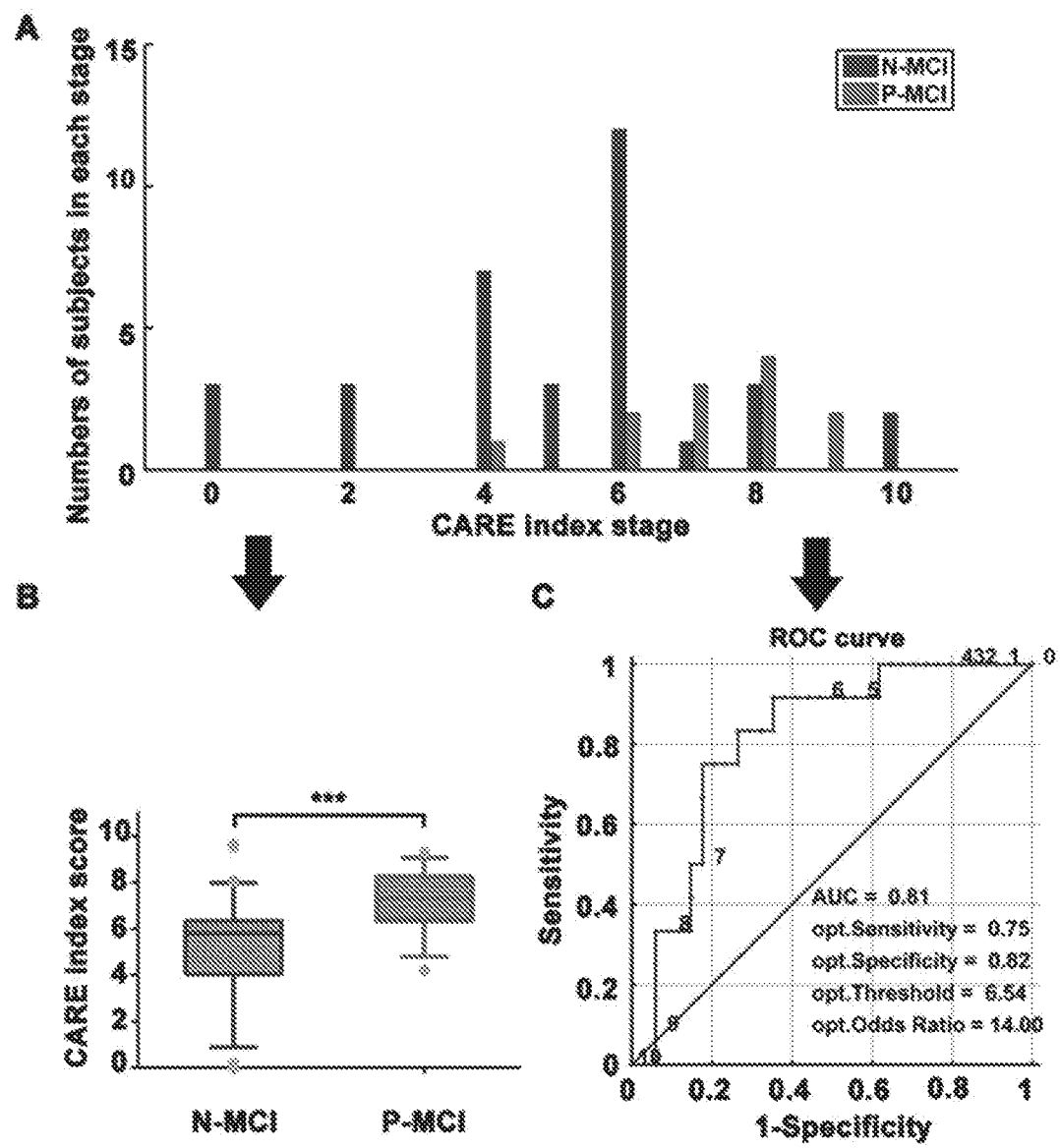
FIGS. 19A-19C show the classification of N-MCI and P-MCI in the ADNI dataset determined by individual CARE index score.

Discrimination N-MCI/P-MCI. To evaluate the CARE index power to discriminate P-MCI from N-MCI, the ADNI dataset and each subject's individual CARE index score were first used to determine how well CARE index can predict outcomes of MCI subjects. As shown in FIGS. 19A-19C, the CARE index as a predictor performed well to discriminate MCI progression to AD with the AUC of 0.81. The optimal threshold of CARE index for discrimination between P-MCI and N-MCI was found at CARE index of 6.54, with the sensitivity of 75.0%, specificity of 82.4%, the OR of 14.0, and RR of 6.20.

Figure 20:
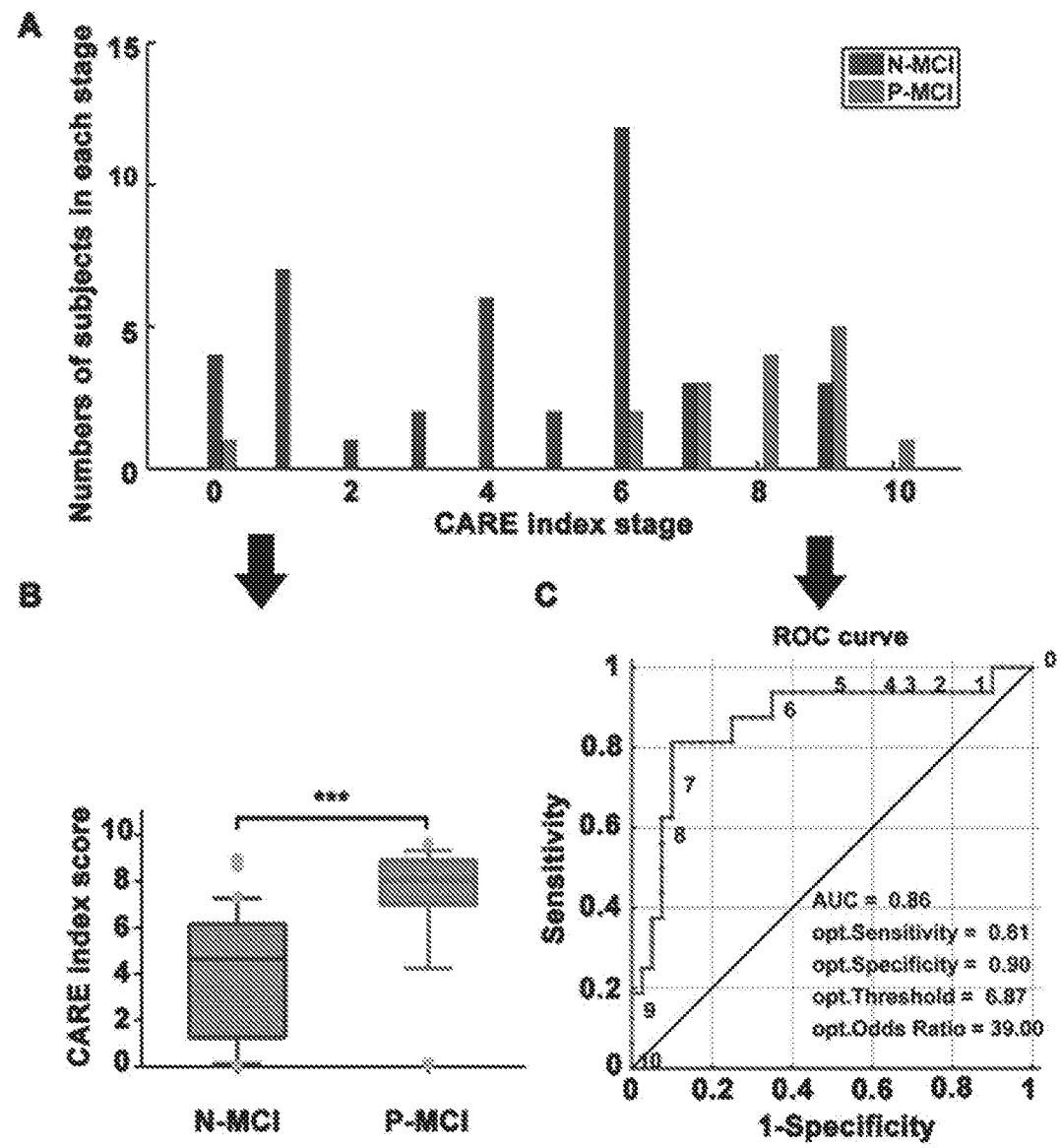
FIGS. 20A-20C show prediction of N-MCI and P-MCI in the NADS dataset using individual CARE index score determined by CARE index threshold.
Figure 21:
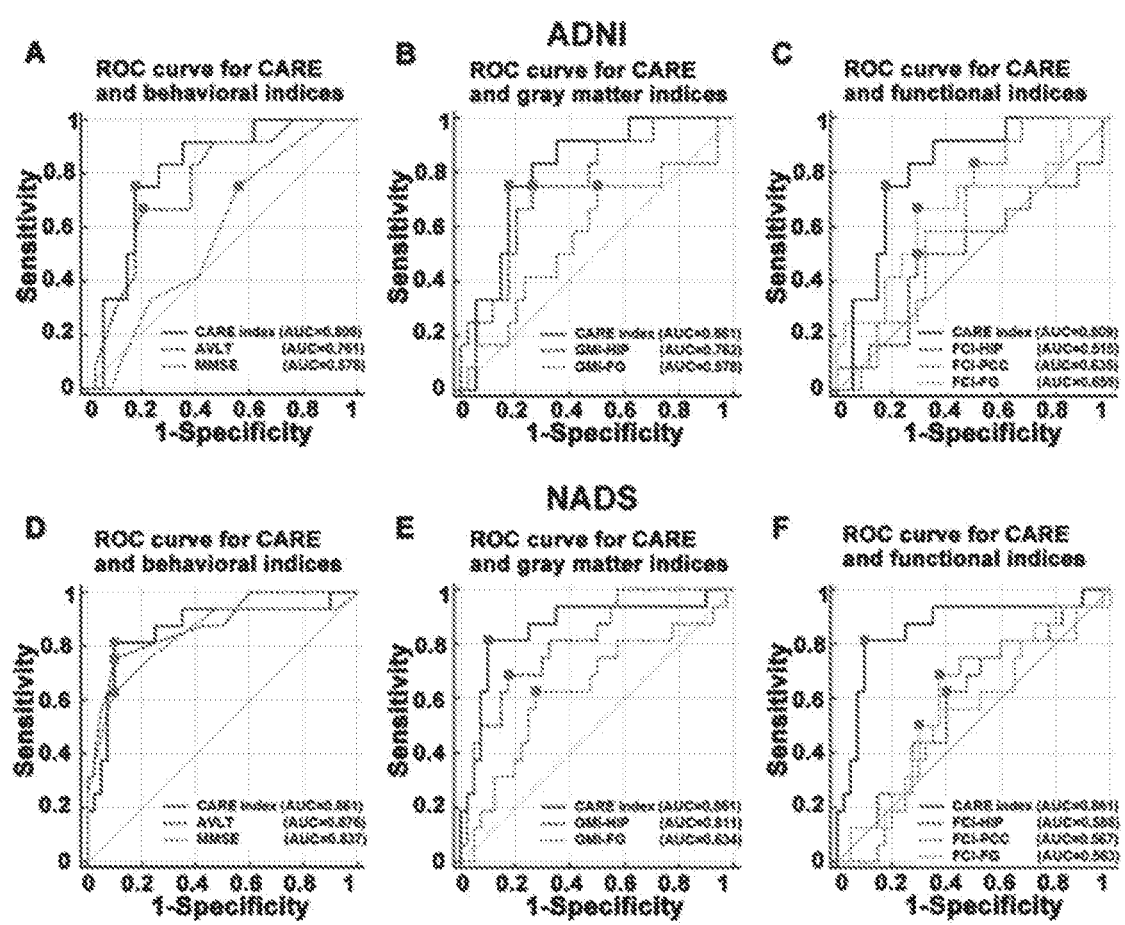
FIGS. 21A-21F show comparisons of the power of ROC curve of CARE index and individual behavioral, gray matter, and functional indices in predicting the P-MCI versus N-MCI at baseline in the ADNI and NADS datasets, respectively.

Robustness in different cohorts. To validate the CARE index robustness to discriminate P-MCI from N-MCI, CARE index staging was applied to MCI subjects in the NADS dataset to determine how well CARE index can predict the conversion outcomes. As shown in FIGS. 20A-20C, it is well validated that the CARE index had significant power to classify P-MCI from N-MCI with AUC of 0.86. At the CARE index of 6.87, t the prediction has high sensitivity (81.3%) and specificity (90.0%), and OR (39.0). When combining both the ADNI and NADS datasets on MCI subjects as a single cohort, supplemental analysis also showed that the CARE index had a very high predictive performance to discriminate P-MCI from N-MCI on individual subject basis, with 83.3% accuracy, 82.0% balanced accuracy, 79% sensitivity, 85% specificity, AUC of 0.84 in ROC on MCI subjects from the ADNI and NADS combined cohort.

Generalization in different cohorts. To validate the generalizability of the CARE index to discriminate P-MCI from N-MCI, we applied the optimal threshold of CARE index in discriminating between P-MCI and N-MCI obtained from the ADNI dataset to the MCI subjects in the NADS dataset. It was found that of the 56 MCI subjects, 48 were predicted correctly with accuracy of 85.7%. MCI subjects having a CARE index above the threshold have high diagnostic odds ratio (OR=33.33, 95% CI: 6.33-145.30) and relative risk (RR=9.15, 95% CI: 2.98-28.13) in MCI progression to AD relative to no-progression to AD (see Table 2). The CARE index showed consistently high performance in different independent datasets and achieved best predictive accuracy, specificity, and sensitivity in both datasets.

Comparison of the discrimination power of CARE index with that of each of the seven selected biomarker indices. The CARE index power to discriminate P-MCI from N-MCI was compared with the discrimination power of each of the seven selected biomarker indices with the 46 MCI subjects in the ADNI dataset and the 56 MCI subjects in the NADS dataset (see FIGS. 21A-21F). In the ADNI dataset, the CARE index performed better than each of the seven selected biomarker indices in discriminating P-MCI from N-MCI. Their AUC range is between 0.49-0.76, sensitivity range 0.50-0.83; specificity range 0.44-0.79. The CARE index ranked first in all biomarkers with 78.7% balanced accuracy. And the HIPGMI score discriminating P-MCI from N-MCI presented a lower specificity of 0.74, accuracy of 73.9%, and balanced accuracy of 74.3% than those of the CARE index (specificity=0.82, accuracy=80.4%, balanced accuracy=78.7%, see FIG. 4 and Table 3). In the NADS dataset, although the best single biomarker index was AVLT score with an AUC of 0.876, the CARE index power in discriminating P-MCI from N-MCI showed high generalization and stability across datasets, whereas other individual biomarkers did not have. For example, when applying the cut-off value of the best single biomarker index (HIPGMI score) in the ADNI dataset to the NADS dataset, the sensitivity and balanced accuracy of the biomarker index dropped from 0.75 to 0.38, and from 74.3 to 66.3, respectively. And the best single biomarker index (AVLT index, accuracy=85.7%, balanced accuracy=82.4%) in the NADS dataset also showed large variability, especially, the accuracy and balanced accuracy dropped to 52.2% and 73.0% in the ADNI dataset, respectively. In contrast, the CARE index showed higher consistency and robustness in discriminating P-MCI from N-MCI when using different and independent datasets.

Figure 22:
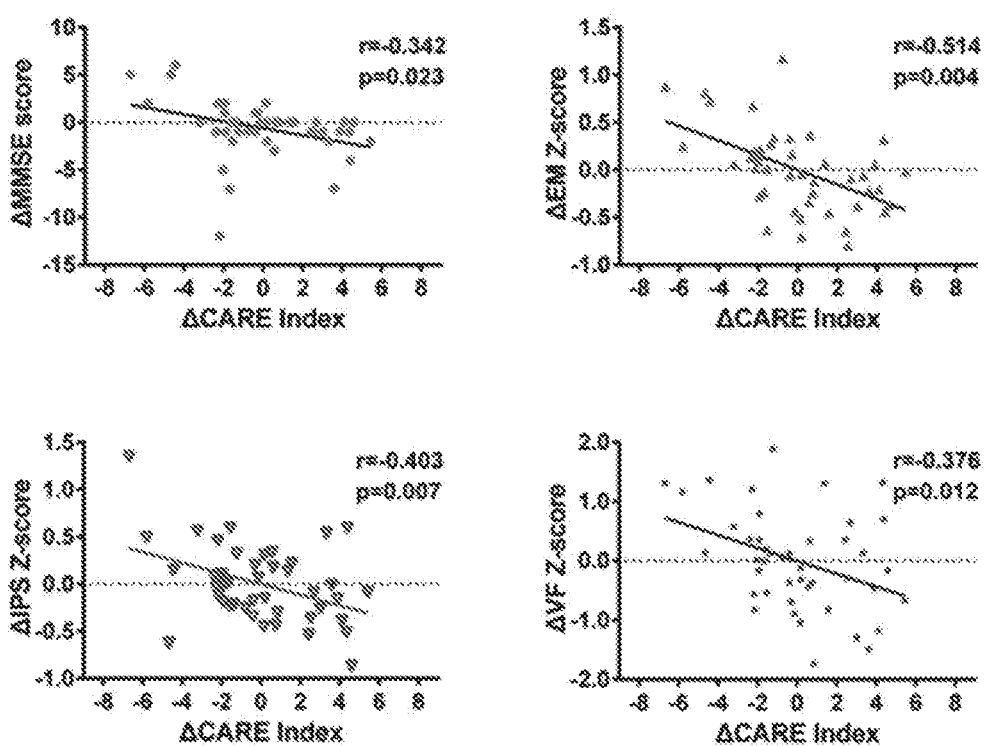
FIG. 22 shows the relationships between the changes in CARE index and changes in cognitive performance or clinical variables measured at baseline and 3-year follow up in MCI subjects from the NADS dataset.

Behavioral significance of the changes in CARE index measured at baseline and 3-year follow-up. The multiple linear regression analysis demonstrated that the changes in CARE index measured at baseline and 3-year follow-up were negatively correlated with changes in MMSE scores and the composite Z scores of episodic memory, information processing speed, and visuospatial function in MCI (p<0.05, see FIG. 22). The higher the CARE index score changed, the more the disease progression advanced. There was no such behavioral correlation for other individual biomarker indices or other cognitive functions in MCI (p>0.05, see FIG. 22).

Example 4

In this example study, the hypothesis that, although the Alzheimer's disease and normal aging processes share similar neurodegenerative events, their CARE index score age trajectories are significantly different was tested. In addition, it was tested whether the APOE ε4 allele significantly modulates the age trajectory of the CARE index score.

Example 4: Methods

Subject information. Data used in this study were obtained from the ADNI-2 database. For this study, 144 subjects were selected, including 45 CN, 74 MCI, and 25 Alzheimer's disease subjects.

EBP model and the CARE index score for each individual subject. The EBP model described above was applied to estimate the $S^{optimal}$ of events in which different biomarkers become abnormal in a temporally ordered manner, using cross-sectional real-world data. In this study, 10 acknowledged Alzheimer's disease biomarkers (i.e., those described above) were selected from three sets of examinations: a neuropsychological assessment, an MRI scan, and CSF.

In brief, the order of the 10 biomarker events in the calibrated $S^{optimal}$ sequence is defined as the CARE index. The CARE index score for each individual subject was obtained from the highest likelihood value among the likelihood values at each event in the $S^{optimal}$ sequence. In this study, only CN and Alzheimer's disease subjects were employed to calibrate the $S^{optimal}$. MCI subjects were treated as an independent dataset, relative to the calibrating processes.

Statistical analysis. One-way ANOVA and chi-square tests were used to compare quantitative and qualitative data, respectively. The Tukey-Kramer post hoc test was employed if any significant among-group differences emerged. The significance level was at $p<0.05$. The random-effect two-sample t-tests compared the CARE index score between the ε4 carriers and non-carriers in each group.

A sigmoidal function, $y=10*e^{(-1)*((a*(x+c))^b+1)}$, was used to calculate the age trajectories of the CARE index score in the CN, MCI, and Alzheimer's disease groups, as well as in the ε4 carriers and non-carriers, respectively. In this sigmoid function, the x is the age bin value, with five years in each bin; each subject's age was converted to the corresponding age bin. The y is the mean CARE index score of the subjects within the age bin. A bootstrap method was used to statistically compare the fitted sigmoid function curves among groups by selecting 100 random samples from each group and fitting the sigmoid curve between the age bin and CARE index scores. The AUC of the fitted curve was calculated. After the above steps were repeated 1000 times, the Wilcoxon signed-rank test was used to compare the difference in AUC values among groups.

Example 4: Results

Subject information. The three groups were comparable in demographic information but exhibited significant differences in cognitive performance; CSF, A, and p-tau levels; and distribution of APOE status.

Figure 23:
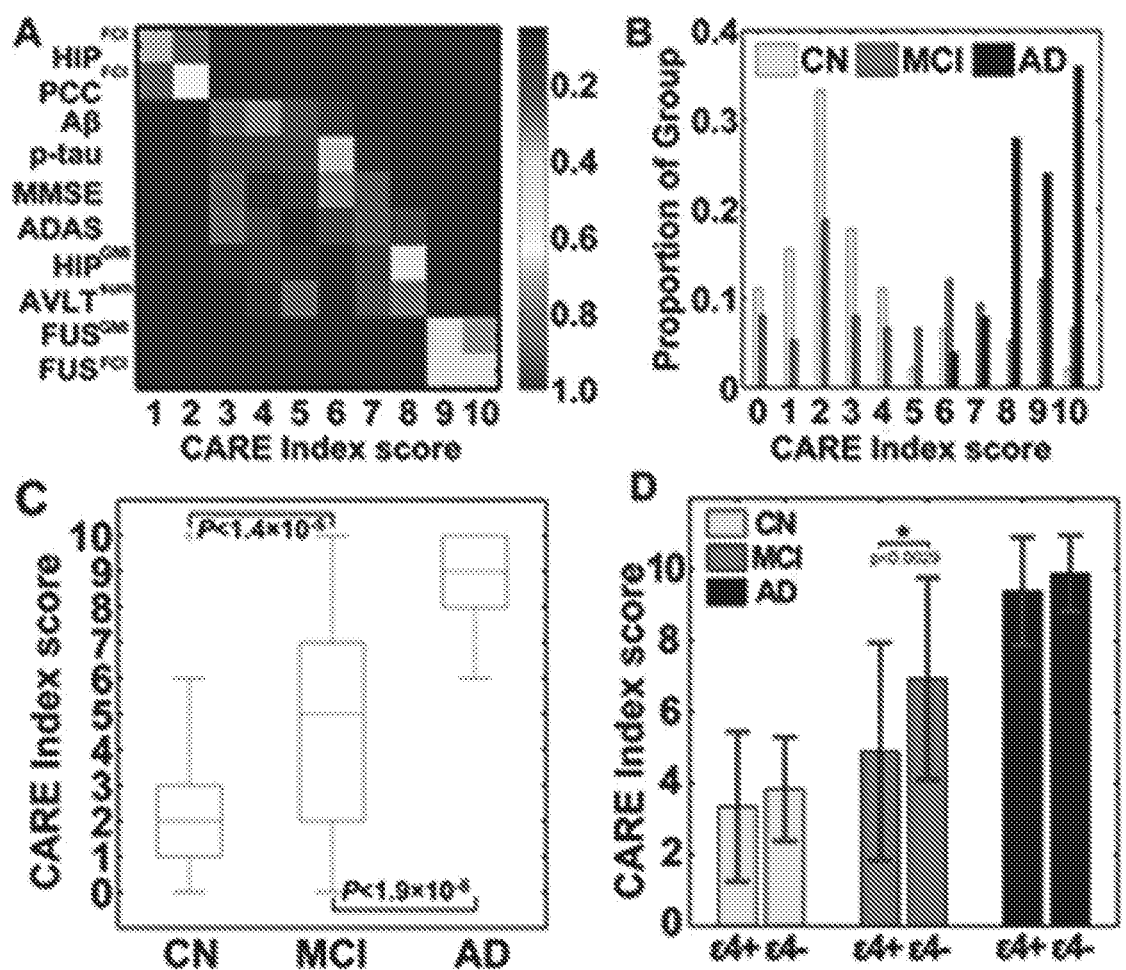
FIGS. 23A-23D show the CARE index and its association with cognitive and APOE status.

The CARE index and its association with clinical and APOE status. FIG. 23A shows the calibrated $S^{optimal}$ of the Alzheimer's disease process across the full continuum from the preclinical stage to overt dementia. The abnormal events occurred first in the HFC (CARE index score 1) and DMN (CARE index sore 2), followed by abnormal CSF levels in Aβ (CARE index score 3) and tau (CARE index score 4). The abnormal subsequent events occurred, in turn, in the order of MMSE, ADAS, hippocampus volume, and AVLT score. Finally, the abnormal events occurred in the fusiform gurus volume and functional connectivity.

According to the $S^{optimal}$, an individual subject's CARE index score can be derived regardless of the subject's own clinical status. It was found that all but one of the CN subjects had a CARE index score lower than six, while all Alzheimer's disease subjects had a CARE index score higher than six; the CARE index scores of the MCI subjects were distributed between those of the CN and Alzheimer's disease groups (FIG. 23B), indicating the biologically heterogeneity of the MCI population. At the group level, the CARE index score significantly increased from the CN to MCI to Alzheimer's disease group (CN vs. MCI: $t=-4.54$, $p<1.4\times10^{-5}$; CN vs. Alzheimer's disease: $t=-14.83$, $p=5.4\times10^{-23}$; MCI vs. Alzheimer's disease: $t=-6.13$, $p<1.9\times10^{-8}$, FIG. 23C). In addition, within the MCI group, the APOE ε4 carriers exhibited significantly higher CARE index scores than the noncarriers ($t=3.09$, $p=0.00^3$, FIG. 23D).

Figure 24:
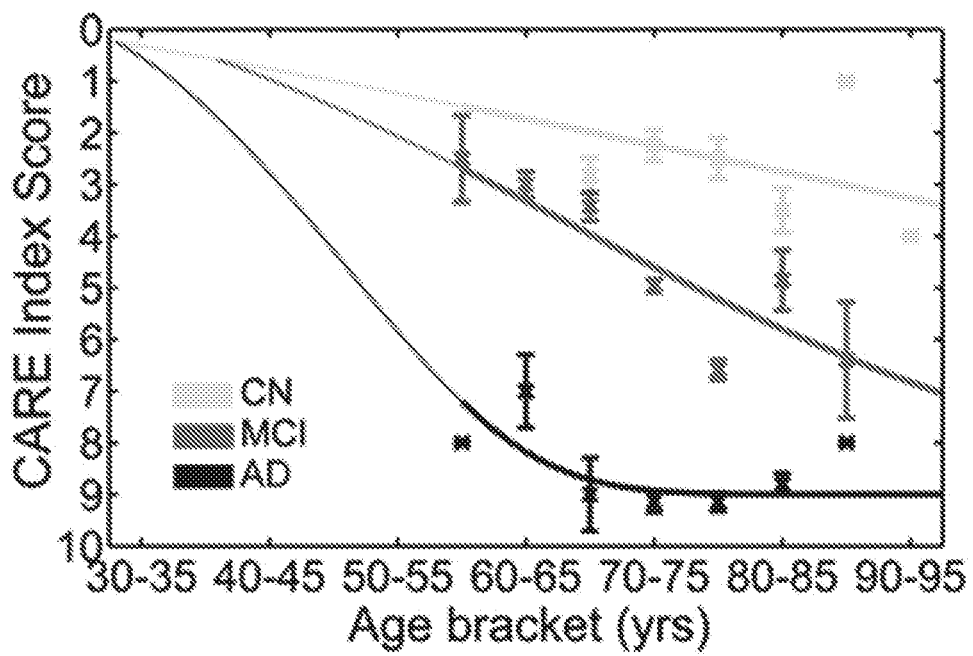
FIG. 24 shows divergent age trajectories of the CARE index score in the CN, MCI, and Alzheimer's disease groups. The CARE index scores show significant nonlinear increases with advancing age in the CN, MCI, and Alzheimer's disease groups, indicated by the sigmoidal functions. Notably, an age-related increase in the CARE index score was most advanced in the Alzheimer's disease group, followed in turn by the MCI and CN groups.

Age trajectory of the CARE index score in each clinical group. The three groups unanimously exhibited age-related increases in their CARE index scores. The AUC values calculated from resampling the 1000 bootstrap samples were significantly lower in the Alzheimer's disease group compared with the CN ($z=21.31$, $p=0$) and MCI groups ($z=2.33$, $p=0.02$). This indicates that the age trajectories of the CARE index can significantly differentiate among the Alzheimer's disease, MCI, and CN groups (FIG. 24), with faster decay in the Alzheimer's disease process, slower decay in the normal aging process, and medium decay in the MCI process. For example, at the age bin of 70-75 years, the estimated CARE index scores in the CN, MCI, and Alzheimer's disease groups were approximately 2, 5, and 9, respectively.

Figure 25:
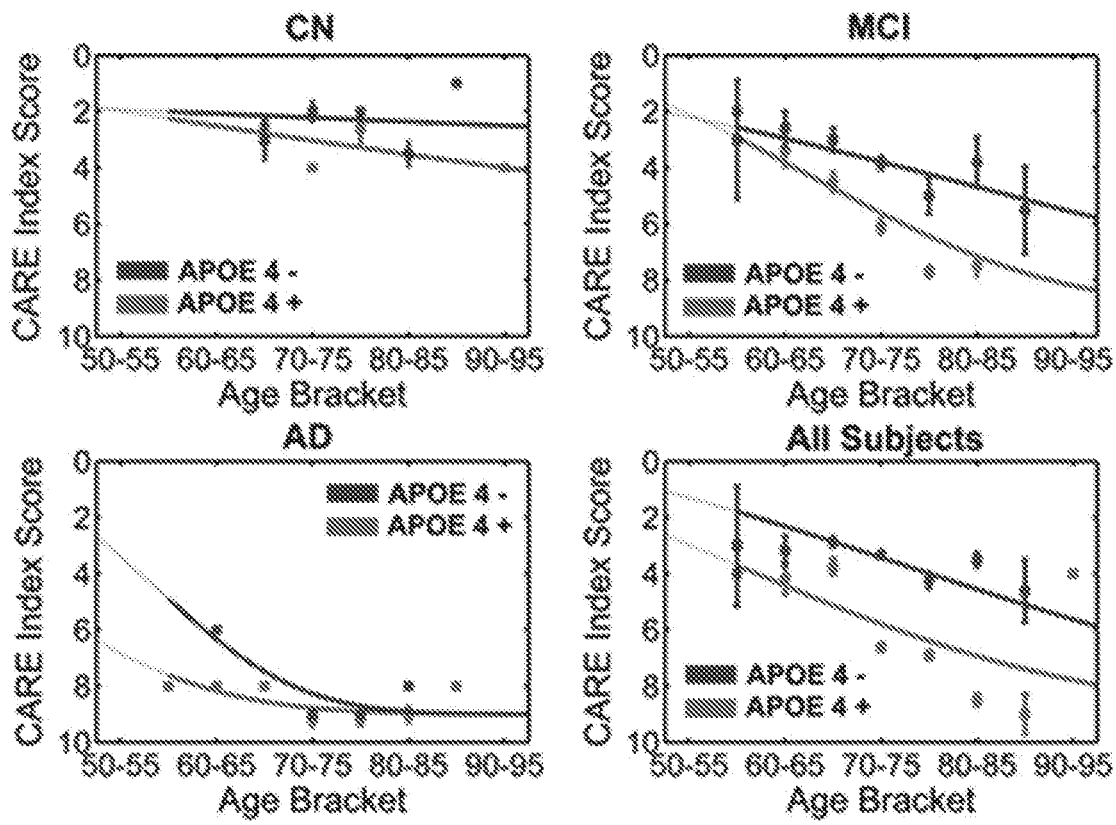
FIG. 25 shows left shift of the age trajectories of the CARE index score by the APOE ε4 allele in the CN, MCI, and Alzheimer's disease groups, and across all subjects. The CARE index scores exhibited an age-related increase in both ε4 carriers and non-carriers. Particularly, the ε4 allele significantly advanced age-related increases in the CARE index score in the MCI and Alzheimer's disease groups, as well as across all subjects.

Left shift in the age trajectories of the CARE index score by the APOE ε4 allele. As shown in FIG. 25, both the APOE ε4 carriers and non-carriers exhibited age-related increases in the CARE index score within each group and across all subjects. Further, the APOE ε4 allele was related to a left shift in the age trajectories: the AUC values were significantly lower in the ε4 carriers compared with the non-carriers within the MCI ($z=12.22$, $p=20.56\times10^{-34}$) and Alzheimer's disease ($z=13.06$, $p=5.64\times10^{-39}$) groups, and across all subjects ($z=12.22$, $p=20.56\times10^{-34}$). This indicates distinguished differences in CARE index trajectories in the ε4 carriers relative to the non-carriers.

The present disclosure has described one or more preferred embodiments, and it should be appreciated that many equivalents, alternatives, variations, and modifications, aside from those expressly stated, are possible and within the scope of the invention.

The invention claimed is:

1. A computer-implemented method for generating a quantitative index value representative of an Alzheimer's disease stage, the steps of the method comprising:
    (a) providing to a computer system, biomarker data obtained from a subject;
    (b) providing to the computer system, an optimal biomarker event sequence representative of a temporally ordered sequence of biomarker events associated with Alzheimer's disease;
    (c) computing with the computer system, a subject-specific risk index value using the optimal biomarker event sequence and the biomarker data; and
    (d) generating a report based on the subject-specific risk index value, wherein the report quantitatively characterizes Alzheimer's disease risk events for the subject.

2. The method as recited in claim 1, further comprising characterizing an Alzheimer's disease progression stage based on the subject-specific risk index value, and wherein the report further provides an indication of the Alzheimer's disease progression stage for the subject.

3. The method as recited in claim 1, wherein step (b) includes determining the optimal biomarker event sequence with the computer system based on the biomarker data.

4. The method as recited in claim 3, wherein determining the optimal biomarker event sequence with the computer system includes:
(i) estimating from the biomarker data, a likelihood of measurements given each of a plurality of possible sequences of biomarker events and a subject's stage;
(ii) computing a likelihood of measurements in a condition of each of the plurality of sequences based on the likelihood of measurements given each of a plurality of possible sequences of biomarker events and a subject's stage; and
(iii) determining the optimal biomarker event sequence based on the likelihood of measurements in the condition of each of the plurality of sequences.

5. The method as recited in claim 4, wherein step (i) includes:
estimating from the biomarker data, a likelihood of a measurement given a biomarker event having occurred;
estimating from the biomarker data, a likelihood of a measurement given a biomarker event having not occurred; and
estimating the likelihood of measurements given each of a plurality of possible sequences of biomarker events and a subject's stage based on the likelihood of a measurement given a biomarker event having occurred and the likelihood of a measurement given a biomarker event having not occurred.

6. The method as recited in claim 4, wherein the likelihood of measurements computed in step (ii) is a normalized likelihood of measurements in the condition of each of the plurality of sequences, and wherein the subject's stage is a weighted average stage.

7. The method as recited in claim 3, wherein determining the optimal biomarker event sequence with the computer system includes determining the optimal biomarker event sequence as a sequence of biomarker events having a maximal likelihood of measuring the provided biomarker data.

8. The method as recited in claim 7, wherein optimal biomarker event sequence with the computer system includes implementing a greedy algorithm to identify the sequence of biomarker events having the maximal likelihood of measuring the provided biomarker data.

9. The method as recited in claim 8, wherein the greedy algorithm includes:
providing a set of initial root sequences each having a number of biomarker events from a list of available biomarker events, wherein the number is smaller than a total number of biomarker events in the list of available biomarker events;
(ii) generating children sequences based on the initial root sequences by inserting a biomarker event from the list of available biomarker events to each initial root sequence;
(iii) updating the initial sequences as the children sequences having the maximal likelihood of measuring the provided biomarker data;
(iv) iteratively repeating steps (ii) and (iii) until all of the available biomarker events have been inserted into the children sequences; and
(v) selecting the optimal sequence of biomarker events as the children sequence having the maximal likelihood of measuring the provided biomarker data.

10. The method as recited in claim 1, wherein the biomarker data includes biomarkers derived from resting-state functional magnetic resonance images of the subject.

11. The method as recited in claim 10, wherein providing the biomarker data to the computer system includes acquiring the resting-state functional magnetic resonance images from the subject using a magnetic resonance imaging system.

12. The method as recited in claim 10, wherein the biomarker data includes functional connectivity indices computed from the resting-state functional magnetic resonance images.

13. The method as recited in claim 10, wherein the biomarker data further includes biomarkers derived from diffusion-weighted magnetic resonance images.

14. The method as recited in claim 10, wherein the biomarker data further includes a cerebral blood flow measurement.

* * * * *